(12) United States Patent
Zheng et al.

(10) Patent No.: US 8,980,563 B2
(45) Date of Patent: Mar. 17, 2015

(54) MULTIPLEX TARGETED AMPLIFICATION USING FLAP NUCLEASE

(75) Inventors: Jianbiao Zheng, Fremont, CA (US); Li Weng, Fremont, CA (US); Malek Faham, Pacifica, CA (US)

(73) Assignee: Affymetrix, Inc., Santa Clara, CA (US)

(*) Notice: Subject to any disclaimer, the term of this patent is extended or adjusted under 35 U.S.C. 154(b) by 464 days.

(21) Appl. No.: 12/972,208

(22) Filed: Dec. 17, 2010

(65) Prior Publication Data

US 2011/0124052 A1  May 26, 2011

Related U.S. Application Data

(63) Continuation of application No. 12/016,195, filed on Jan. 17, 2008, now Pat. No. 7,862,999.

(60) Provisional application No. 60/885,333, filed on Jan. 17, 2007, provisional application No. 60/887,546, filed on Jan. 31, 2007.

(51) Int. Cl.
*C12Q 1/68* (2006.01)
*C12P 19/34* (2006.01)

(52) U.S. Cl.
CPC .................................. *C12Q 1/6844* (2013.01)
USPC ........................................ 435/6.12; 435/91.2

(58) Field of Classification Search
None
See application file for complete search history.

(56) References Cited

U.S. PATENT DOCUMENTS

| | | | |
|---|---|---|---|
| 5,185,243 A | 2/1993 | Ullman et al. | |
| 5,427,930 A * | 6/1995 | Birkenmeyer et al. | 435/91.52 |
| 5,565,340 A | 10/1996 | Chenchik et al. | |
| 5,582,989 A | 12/1996 | Caskey et al. | |
| 5,843,669 A | 12/1998 | Kaiser et al. | |
| 5,846,717 A | 12/1998 | Brow et al. | |
| 5,871,921 A | 2/1999 | Landegren et al. | |
| 6,350,580 B1 | 2/2002 | Sorge | |
| 7,074,564 B2 | 7/2006 | Landegren et al. | |
| 7,108,976 B2 | 9/2006 | Jones et al. | |
| 7,208,295 B2 | 4/2007 | Faham et al. | |
| 2002/0137036 A1 | 9/2002 | Sorge et al. | |
| 2003/0096291 A1 | 5/2003 | Faham et al. | |
| 2003/0104459 A1 | 6/2003 | Faham et al. | |
| 2005/0037356 A1 | 2/2005 | Gullberg et al. | |
| 2005/0069991 A1* | 3/2005 | Hyman | 435/91.2 |
| 2005/0287526 A1 | 12/2005 | Landegren et al. | |
| 2006/0166235 A1 | 7/2006 | Hennessy et al. | |
| 2007/0128635 A1 | 6/2007 | Macevicz | |

OTHER PUBLICATIONS

Stewart et al. Flap endonuclease disengages Dna2 helicase/nuclease from Okazaki fragment flaps. J. Biol. Chem. (2006) vol. 281, No. 50, pp. 38565-38572.*

Dahl F et al. (2005) Multiplex amplification enabled by selective circularization of large sets of genomic DNA fragments. Nucleic Acids Res. 33, e71.
Faham M. et al. (2005) Multiplexed variation scanning for 1,000 amplicons in hundreds of patients using mismatch repair detection (MRD) on tag arrays. Proc. Natl. Acad. Sci. USA 102:14712-14722.
Fredriksson et al. Multiplex amplification of all coding sequences within 10 cancer genes by Gene-Collector. Nucleic Acids Res. 35(7):e47 (2007).
Guy CP et al(2004) A novel nuclease-ATPase (Nar71) from archaea is part of a proposed thermophilic DNA repair system. Nucleic Acids Res. 32:6176-6186.
Hardenbol et al. Highly multiplexed molecular inversion probe genotyping: over 10,000 targeted SNPs genotyped in a single tube assay. Genome Res. 15,269-275 (2005).
Harrington JJ and Lieber MR (1995) DNA structural elements required for FEN-1 binding. J. Biol. Chem. 270:4503-4508.
Hiraoka LR et al. (1995) Sequence of human FEN-1, a structure-specific endonuclease, and chromosomal localization of the gene (FENI) in mouse and human. Genomics 25:220-225.
Holland PM et al. (1991) Detection of specific polymerase chain reaction product by utilizing the 5'-3' exonuclease activity of Thermus aquaticus DNA polymerase. Proc. Natl. Acad. Sci. USA 88:7276-7280.
Kaiser MW et al. (1999) A comparison of eubacterial and archaeal structure-specific 5'—exonucleases. J. Biol. Chem. 274: 21387-21394.
Kao HI et al. (2002) cleavage specificity of *Saccharomyces cerevisiae* flap endonuclease 1 suggestes a double-flap structure as the cellular substrate. J. Biol. Chem. 277:14379-14389.
Kao HI, et al. (2004) On the roles of *Saccharomyces cerevisiae* Dna2p and Flap endonuclease 1 in Okazaki fragment processing. J. Biol. Chem. 279(15):15014-24.
Lyamichev et al. Comparison of the 5' nuclease activities of Taq DNA polymerase and its isolated nuclease domain, Proc. Nat. Acad. Sci. USA 96:6143-6148 (1999).
Matsui E et al. (2004) Aromatic residues located close to the active center are essential for the catalytic reaction of flap endonuclease-I from hyperthermophilic archaeon *Pyrococcus horikoshii*. J. Biol. Chem. 279:16687-16696.
Nilsson et al. Analyzing genes using closing and replication circles. Trends in Biotech. 24(2):83-88, (2006).
Nishino T, Ishino Y and Morikawa K., Structure-specific DNA nucleases: Structural basis for 3D-scissors. Curr. Op. Struct. Bio. 16: 60-67 (2006).

(Continued)

*Primary Examiner* — Kenneth R. Horlick
*Assistant Examiner* — David Thomas
(74) *Attorney, Agent, or Firm* — Banner & Witcoff, Ltd.

(57) ABSTRACT

Methods for multiplex amplification of a plurality of targets of distinct sequence from a complex mixture are disclosed. In one aspect targets are circularized using a single circularization probe that is complementary to two regions in the target that flank a region to be amplified. The targets may hybridize to the circularization probe so that 5' or 3' flaps are generated and methods for removing flaps and circularizing the resulting product are disclosed. In another aspect targets are hybridized to dU probes so that 5' and 3' flaps are generated. The flaps are cleaved using 5' or 3' flap endonucleases or 3' to 5' exonucleases. The target sequences are then ligated to common primers, the dU probes digested and the ligated targets amplified.

19 Claims, 8 Drawing Sheets

(56) References Cited

OTHER PUBLICATIONS

Pemov A et al. (2005) DNA analysis with multiplex microarray-enhanced PCR. Nucleic Acids Res. 33: e11.

Porreca GJ, Multiplex amplification of large sets of human exons. Nat. Methods 4(11):931-6. Epub Oct. 14, 2007.

Rubin, et al. (1995) Convergent DNA synthesis: A non-enzymatic dimerization approach to circular oligodeoxynucleotides. Nuc. Acids Res., 23:3547-3553.

Shapero MH et al. (2001) SNP genotyping by multiplexed solid-phase amplification and fluorescent minisequencing. Genome Res. 11: 1926-1934.

Shapero MH et al. (2004) MARA: a novel approach for highly multiplexed locus-specific SNP genotyping using high-density DNA oligonucleotide arrays. Nucleic Acids Res. 32: e181.

Sijbers AM et al. (1996) Xeroderma Pigmentosum Group F caused by a defect in a structure-specific DNA repair endonuclease. Cell 86: 811-822.

Stenberg et al., PieceMaker: selection of DNA fragments for selector-guided multiplex amplification, Nuc. Acids Res. 33:8 e72 (2005).

Wang H-Y et al. (2005) A genotyping system capable of simultaneously analyzing >1000 single nucleotide polymorphisms in a haploid genome. Genome Res. 15: 276-283.

* cited by examiner

SEQUENCE LISTING

```
<160> NUMBER OF SEQ ID NOS: 7

<210> SEQ ID NO 1
<211> LENGTH: 50
<212> TYPE: DNA
<213> ORGANISM: Artificial
<220> FEATURE:
<223> OTHER INFORMATION: Synthetic

<400> SEQUENCE: 1
agagtcctat ggctggttca tgcaagctgc cggagtgaac gctgagtgag          50

<210> SEQ ID NO 2
<211> LENGTH: 39
<212> TYPE: DNA
<213> ORGANISM: artificial
<220> FEATURE:
<223> OTHER INFORMATION: Synthetic

<400> SEQUENCE: 2
ctcactcagc gttcactccg gcagcttgcc tgtactgtt                      39

<210> SEQ ID NO 3
<211> LENGTH: 38
<212> TYPE: DNA
<213> ORGANISM: artificial
<220> FEATURE:
<223> OTHER INFORMATION: Synthetic

<400> SEQUENCE: 3
gtgtttgtgc gttttgcatg aaccagccat aggactct                       38

<210> SEQ ID NO 4
<211> LENGTH: 28
<212> TYPE: DNA
<213> ORGANISM: artificial
<220> FEATURE:
<223> OTHER INFORMATION: Synthetic

<400> SEQUENCE: 4
ctcactcagc gttcactccg gcagcttg                                  28

<210> SEQ ID NO 5
```

```
<211> LENGTH: 16
<212> TYPE: DNA
<213> ORGANISM: artificial
<220> FEATURE:
<223> OTHER INFORMATION: Synthetic

<400> SEQUENCE: 5
gtgtttgtgc gttttg                                                    16

<210> SEQ ID NO 6
<211> LENGTH: 22
<212> TYPE: DNA
<213> ORGANISM: artificial
<220> FEATURE:
<223> OTHER INFORMATION: Synthetic

<400> SEQUENCE: 6
catgaaccag ccataggact ct                                             22

<210> SEQ ID NO 7
<211> LENGTH: 49
<212> TYPE: DNA
<213> ORGANISM: artificial
<220> FEATURE:
<223> OTHER INFORMATION: Synthetic

<400> SEQUENCE: 7
ctcactcagc gttcactccg cagcttgcat gaaccagcca taggactct                49
```

MULTIPLEX TARGETED AMPLIFICATION USING FLAP NUCLEASE

RELATED APPLICATIONS

This application is a continuation application of U.S. patent application Ser. No. 12/016,195, filed Jan. 17, 2008, now U.S. Pat. No. 7,862,999, which claims the benefit of U.S. Provisional Patent Application Ser. Nos. 60/885,333, filed Jan. 17, 2007 and 60/887,546, filed Jan. 31, 2007, which are incorporated herein by reference in their entireties for all purposes.

FIELD OF THE INVENTION

The invention is related to methods for amplifying a plurality of specific targets in a multiplex amplification reaction.

BACKGROUND OF THE INVENTION

Over the past two decades, the in vitro amplification of specific nucleic acids has become an essential tool for molecular biologists. More recently, multiplexed amplification, in which a plurality of nucleic acid sequences are amplified in a single reaction, Chamberlain et al., *Nucl. Acid Research* 16(23):11141-1156 (1988); U.S. Pat. No. 5,582,989, has become increasingly important. For example, multiplexed amplification, particularly multiplexed polymerase chain reaction (PCR), has been used to provide genetic fingerprints of infectious disease organisms. Other applications, such as multiplex SNP genotyping and variation scanning (for example, by mismatch repair detection), also greatly benefit from PCR multiplexing.

In its original implementation, multiplex PCR reactions include a specific primer pair for each locus to be amplified. These approaches have been plagued with problems, however, including uneven or failed amplification of some templates (especially those having GC rich-sequences), preferential amplification of other templates, poor sensitivity and specificity, poor reproducibility, and the generation of spurious amplification products (Henegariu et al., *BioTechniques* 23(3): 504-511 (1997); Markoulatos et al., *J. Clin. Lab. Anal.* 16: 47-51 (2002)).

Various modifications to the original approach have been developed in efforts to minimize these problems. Among these modifications are changes to the reaction conditions, including adjustment of primer concentrations, $MgCl_2$ and dNTP concentrations, changes in PCR buffer concentrations, balance between $MgCl_2$ and dNTP concentrations, amounts of template DNA and Taq DNA polymerase, extension and annealing time and temperature, and the addition of adjuvants (Henegariu et al., BioTechniques 23(3): 504-511 (1997); Markoulatos et al., J. Clin. Lab. Anal. 16: 47-51 (2002)). Other strategies used include subcycling temperatures between high and low temperatures below the denaturation temperature, used during the annealing and elongation steps (U.S. Pat. No. 6,355,422), and the use of one sequence-specific primer and one common primer (Broude et al., Proc. Natl. Acad. Sci. USA 98, 206-211 (2001))

The intractability of GC-rich sequences to multiplex PCR has also been addressed by a method in which addition of betaine and dimethylsulfoxide (DMSO) to the PCR reaction mix is said to allow more uniform amplification from a heterogeneous population of DNA molecules, many of which were GC-rich (Baskaran et al., Genome Research 6: 633-638 (1996)).

Yet other approaches alter the primers. In one such effort, chimeric oligonucleotides are used as primers: the oligonucleotides include a 3' domain that is complementary to template, conferring template specificity, and a 5' domain that is noncomplementary to template; the 5' domain includes a sequence used to prime extension in rounds of PCR amplification subsequent to the first. In this latter scheme, however, the cycles of amplification following the first amplify whatever product is generated in the first cycle, whether correct or erroneous. Thus, while the technique allows for more uniform amplification, it does not address the problem of spurious products.

In an analogous approach designed to clone the shared components in two complex samples, Brookes et al., *Human Molec. Genetics* 3(11):2011-2017 (1994), ligate primers to template ends generated by restriction fragment digestion. None of the above-mentioned approaches, however, fully solves the problems associated with multiplex PCR. Thus, there is a continuing need in the art for a method that allows the specific and uniform amplification of multiple nucleic acid sequences in a single reaction, without the generation of spurious products.

Multiplex targeted genome amplification allows simultaneous generation of many targets in the same tube for cost-effective genotyping, sequencing or resequencing. The most powerful targeted amplification has been the polymerase chain reaction (PCR). Traditional multiplex PCR has been used to amplify two or more targets by putting multiple pairs of primers simultaneously in the same reaction. However, due to exponential increase in primer-dimer interaction when more pairs of primers are included as well as unequal amplification rates among different amplicons, the multiplexing level of this traditional scheme is typically efficient for up to about 20-plex, often with individual primer concentrations requiring adjustment. This scheme has found applications in multiplex real time PCR or microsatellite amplification and commercial kits, for example, from Qiagen, are available.

Current amplification methods range from non-specific amplification of the entire genome, for example, whole genome amplification (WGA) methods such as MDA, to highly targeted PCR amplification of a few or a single selected region of, for example, a few kb. Methods that result in amplification of a reproducible subset of a genome, for example, the Affymetrix whole genome sampling assay (WGSA) may also be used to amplify genomic material for downstream analysis. The WGA methods generally result in a non-selective amplification of the entire genome. The WGSA method results in amplification of a selected subset of the genome, the subset being defined by the restriction enzyme or enzymes used for cutting the DNA prior to adapter-mediated PCR amplification. Other methods that allow targeted amplification of large numbers of specific targets include, for example, the With whole genome amplification methods being applied to amplifying the whole human genome (a few billion bp) at one end and PCR in targeting a few kb sequences in the other end, there is a need to have a strategy amplifying 1-100 million by that can cover exons and promoter regions of most or all the functional genes.

Attempts have been made over the years since the invention of PCR to increase the multiplex level of PCR. Some of the strategies include two-stage PCR with universal tails (Lin Z et al., PNAS 93: 2582-2587, 1996; Brownie J. et al., Nucleic Acids Res. 25: 3235-3241, 1997), solid-phase multiplex PCR (e.g., Adams and Kron, U.S. Pat. No. 5,641,658; Shapero et al., Genome Res. 11: 1926-1934, 2001), multiplexed anchored runoff amplification (MARA, Shapero et al., Nucleic Acid Res. 32: e181, 2004 and U.S. Pat. No. 7,108, 976), PCR with primers designed by a special bioinformatical tool (Wang et al., Genome Res. 15: 276, 2005), selector-guided multiplex amplification (Dahl F et al., Nucleic Acids Res. 33: e71, 2005), and dU probe-based multiplex PCR after common oligo addition (Faham M and Zheng J, U.S. Pat. No. 7,208,295 and Faham M et al., PNAS 102: 14717-14722, 2005). However, most of above strategies are either work most efficiently at about 100 to 1000-plex, or suffer low efficiency, with the exception of the last two strategies that are potentially scalable to over 10,000-plex (or over a million bp). The method of Dahl et al. requires synthesis of long oligo probes (usually >80 bases) and the method of Faham et al. requires synthesis of dU probes by PCR for each target (Faham M et al., 2005). Multiplex PCR methods are also disclosed in U.S. Patent publication Nos. 20030104459. See also, Nilsson et al., Trends. Biotechnol. 24(2):83-8, 2006 and Stenberg et al., NAR 33(8):e72, 2005.

SUMMARY OF THE INVENTION

Methods for multiplex amplification are disclosed. In general the methods include fragmentation of targets, circularization of targets using juxtaposition of the ends of the target using a splinting circularization probe and ligation of the ends of the targets.

In one embodiment the fragment ends are of known sequence and the circularization probe is designed to juxtapose the ends so that they can be ligated.

In another embodiment the circularization probe hybridizes to the target so that a 5' flap is formed and a 3' single base overhang. A 5' flap nuclease is used to remove the 5' flap and to generate juxtaposed ends for ligation.

In another embodiment a 3' flap structure is formed by hybridization of the circularization probe and a 3' flap nuclease is used to remove the 3' flap and the ends are ligated. DNA polymerase and a subset of dNTPs may be added.

In another embodiment both a 5' and a 3' flap are formed and a 3' to 5' exonuclease and a 5' flap nuclease are used to remove the flaps so that the resulting juxtaposed ends can be ligated using a ligase.

The resulting circular targets can be amplified using rolling circle amplification and the amplified targets can be analyzed, for example, by hybridization to an array of probes.

A collection of more than 100, 1,000, 10,000 or 50,000 different sequence targets may be amplified in a single multiplex reaction and the amplification products may be analyzed for genotype, copy number, methylation, translocation, or sequence, for example. Kits for circularization are also contemplated. The kits may contain one or more of the following: a collection of more than 100, 1,000, 10,000 or 50,000 circularization probes, a 3' flap nuclease, a 5' flap nuclease, a ligase, a DNA polymerase, one or more dNTPs, primers for RCA, a Phi29 DNA polymerase and a 3' to 5' exonuclease. In some aspects computer software is used to design the circularization probes based on the fragmentation method, the target genome and the target sequences.

In a preferred aspect a kit that includes at least 100, 1000, 10,000 or 50,000 different circularization probes for amplification of a plurality of target sequences is disclosed. The kit preferably also includes circularization probes, including one for each target to be amplified, a ligase and a flap endonuclease that may be selected from a 5' flap endonuclease and a 3' flap endonuclease, a 3' to 5' exonuclease or a DNA polymerase and one or more dNTPs.

Methods for multiplex amplification of selected targets are also disclosed. In one embodiment a uracil containing probe (dU probe) is generated for each target sequence to be amplified. The DNA sample from which the targets are to be amplified is fragmented to generate target fragments that contain the target sequences. The target fragments also contain extra sequence at either the 5' end, the 3' end or at both the 5' and 3' ends. The target fragments are hybridized to the dU probes, which also contain flanking common sequences at the 5' and 3' ends. When the target fragments are hybridized to the dU probes 5' or 3' flaps are created.

In one embodiment a 5' flap endonuclease is used to remove a 5' flap. In another embodiment a 3' flap endonuclease is used to remove a 3' flap, a DNA polymerase and one or more dNTPs may be included to fill any gaps created. After flap removal common oligonucleotide sequences are ligated to the target sequences at both the 5' and 3' ends and the target sequences are amplified using primers to the common sequences.

The dU probes are typically digested prior to amplification of the target sequences by treatment with UDG and heat or an AP endonuclease.

In one aspect a 3' to 5' exonuclease is used to remove 3' flaps.

BRIEF DESCRIPTION OF THE DRAWINGS

The above and other objects and advantages of the present invention will be apparent upon consideration of the following detailed description taken in conjunction with the accompanying drawings, in which like characters refer to like parts throughout, and in which.

Figure 1:
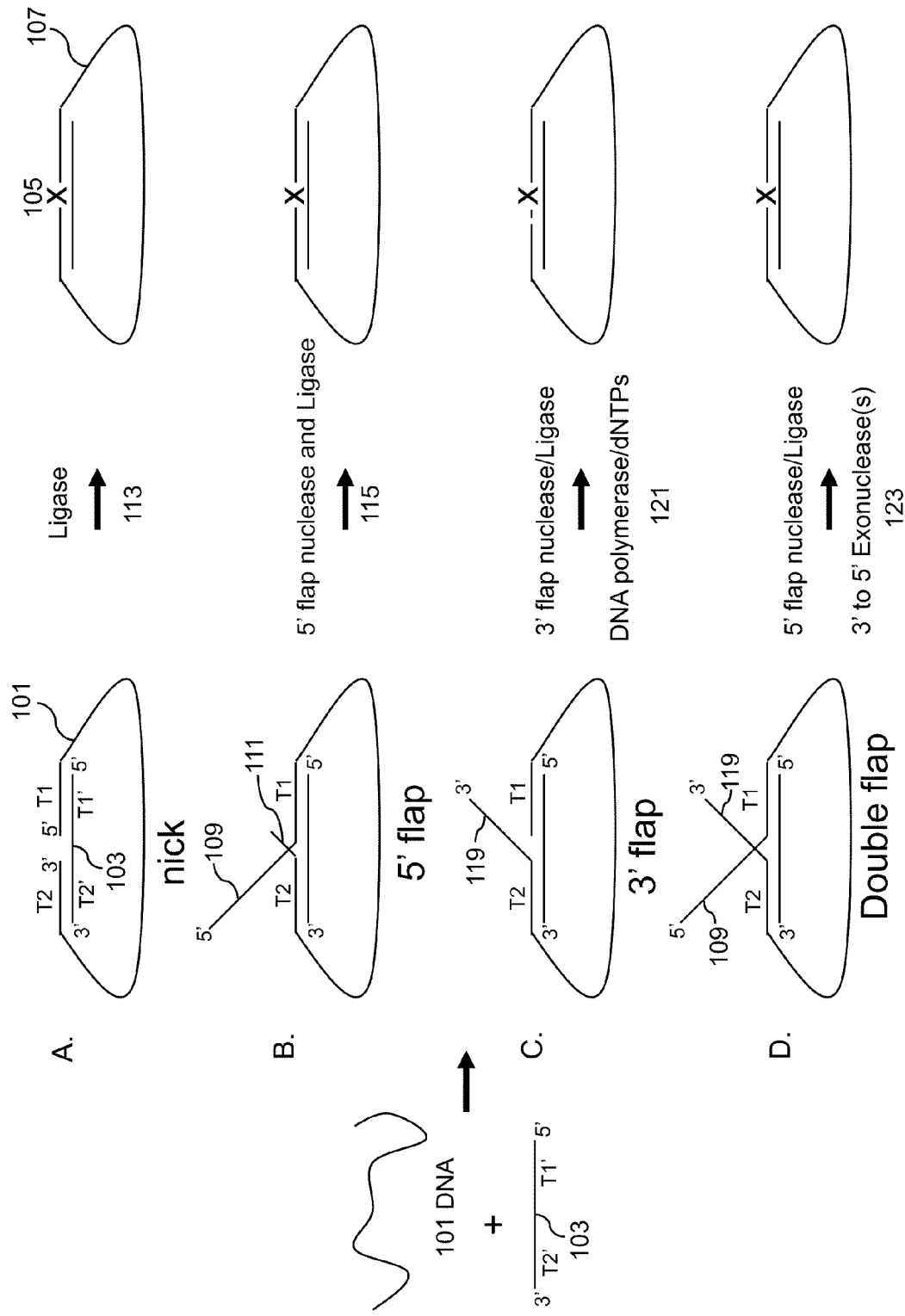
FIG. 1 shows a schematic of four different embodiments of a multiplex amplification method.

DETAILED DESCRIPTION OF THE INVENTION a) General

Reference will now be made in detail to exemplary embodiments of the invention. While the invention will be described in conjunction with the exemplary embodiments, it will be understood that they are not intended to limit the invention to these embodiments. On the contrary, the invention is intended to cover alternatives, modifications and equivalents, which may be included within the spirit and scope of the invention.

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being, but may also be other organisms including, but not limited to, mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series (Vols. I-IV), Using Antibodies: A Laboratory Manual, Cells: A Laboratory Manual, PCR Primer: A Laboratory Manual*, and *Molecular Cloning: A Laboratory Manual*(all from Cold Spring Harbor Laboratory Press), Stryer, L. (1995) *Biochemistry* (4th Ed.) Freeman, New York, Gait, "Oligonucleotide Synthesis: A Practical Approach" 1984, IRL Press, London, Nelson and Cox (2000), *Lehninger, Principles of Biochemistry* $3^{rd}$ Ed., W.H. Freeman Pub., New York, N.Y. and Berg et al. (2002) *Biochemistry*, $5^{th}$ Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Patent Pub. No. 20050074787, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication No. WO 99/36760) and PCT/US01/04285 (International Publication No. WO 01/58593), which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. patent application Ser. No. 10/442,021, U.S. Patent Publication No. 20030036069 and U.S. Pat. Nos. 5,856,092, 6,300, 063, 5,858,659, 6,284,460, 6,361,947, 6,368,799 and 6,333, 179. Other uses are embodied in U.S. Pat. Nos. 5,871,928, 5,902,723, 6,045,996, 5,541,061, and 6,197,506.

The present invention also contemplates sample preparation methods in certain preferred embodiments. Prior to or concurrent with genotyping, the genomic sample may be amplified by a variety of mechanisms, some of which may employ PCR. See, for example, *PCR Technology: Principles and Applications for DNA Amplification* (Ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (Eds. McPherson et al., IRL Press, Oxford); and U.S. Pat. Nos. 4,683,202, 4,683,195, 4,800,159, 4,965, 188, and 5,333,675, each of which is incorporated herein by reference in their entireties for all purposes. The sample may be amplified on the array. See, for example, U.S. Pat. No. 6,300,070 and U.S. Ser. No. 09/513,300, which are incorporated herein by reference.

Methods are disclosed for identifying chromosomal gains and losses at high resolution using high-density microarray genotyping methods such as whole genome sampling analysis (WGSA) (see, Kennedy et al. (2003), *Nat Biotechnol*, Vol., pp. 1233-1237, U.S. Pat. No. 6,361,947, U.S. Patent Publication Nos. 20030025075, 20020142314, 20040146890, 20030186279, 20040072217, 20030186280, and 20040067493 and U.S. patent application Ser. No. 10/442, 021). WGSA simultaneously genotypes more than 10,000 SNPs in parallel by allele-specific hybridization to perfect match (PM) and mismatch (MM) probes synthesized on an array. Methods for chromosomal copy number analysis using the Affymetrix Mapping 10K array in combination with WGSA, have also been reported in Bignell et al. *Genome Res.* 14:287-295 (2004) and Huang et al., *Hum Genomics* 1:287- 299 (2004). Similar analysis using the Affymetrix Mapping 100K array has also been reported in Slater et al., *Am. J. Hum. Genet.* 77:709-726 (2005).

The Whole Genome Sampling Assay (WGSA) reduces the complexity of a nucleic acid sample by amplifying a subset of the fragments in the sample. A nucleic acid sample is fragmented with one or more restriction enzymes and an adapter is ligated to both ends of the fragments. A primer that is complementary to the adapter sequence is used to amplify the fragments using PCR. During PCR fragments of a selected size range are selectively amplified. The size range may be, for example, 400-800 or 400 to 2000 base pairs. Fragments that are outside the selected size range are not efficiently amplified.

The fragments that are amplified by WGSA may be predicted by in silico digestion and an array may be designed to genotype SNPs that are predicted to be amplified. Genotyping may be done by allele specific hybridization with probes that are perfectly complementary to individual alleles of a SNP. A set of probes that are complementary to the region surrounding each SNP may be present on the array. Perfect match probes are complementary to the target over the entire length of the probe. Mismatch probes are identical to PM probes except for a single mismatch base. The mismatch position is typically the central position so for a 25 base probe the mismatch is position 13.

The methods may be combined with other methods of genome analysis and complexity reduction. Other methods of complexity reduction include, for example, AFLP, see U.S. Pat. No. 6,045,994, which is incorporated herein by reference, and arbitrarily primed-PCR (AP-PCR) see McClelland and Welsh, in *PCR Primer: A laboratory Manual*, (1995) eds. C. Dieffenbach and G. Dveksler, Cold Spring Harbor Lab Press, for example, at p 203, which is incorporated herein by reference in its entirety. Additional methods of sample preparation and techniques for reducing the complexity of a nucleic sample are described in Dong et al., *Genome Research* 11, 1418 (2001), in U.S. Pat. Nos. 6,361,947, 6,391,592, 6,458,530 and U.S. Patent Publication Nos. 20030039069, 20050079536, 20030096235, 20030082543, 20040072217, 20050142577, 20050233354, 20050227244, 20050208555, 20050074799, 20050042654 and 20040067493, which are incorporated herein by reference in their entireties.

The design and use of allele-specific probes for analyzing polymorphisms is described by e.g., Saiki et al., *Nature* 324, 163-166 (1986); Dattagupta, EP 235,726, and WO 89/11548. Allele-specific probes can be designed that hybridize to a segment of target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles.

Methods for determining copy number using high density SNP genotyping arrays using the Affymetrix 10K SNP genotyping array and the 100K Mapping Set are disclosed. The methods should also be useful for estimating copy number along with a higher density genotyping array, such as the 500K Mapping Set. The 10K array and the 100K array set use a WGSA target preparation scheme in which single primer PCR amplification of specific fractions of the genome is carried out. The 100K WGSA method uses two separate restriction enzymes that each generates a complexity fraction estimated to be about 300 Mb. The 10K array uses a single restriction enzyme and generates a sample with less than 300 Mb complexity. Both arrays have been shown to genotype SNPs, with call rates, reproducibility, and accuracy greater than 99%, 99.7%, and 99.7% respectively (Matsuzaki et al. Nat Methods 1:109-111, 2004).

The term "WGSA (Whole Genome Sampling Assay) Genotyping Technology" refers to a technology that allows the genotyping of thousands of SNPs simultaneously in complex DNA without the use of locus-specific primers. WGSA reduces the complexity of a nucleic acid sample by amplifying a subset of the fragments in the sample. In this technique, a nucleic acid sample is fragmented with one or more restriction enzyme of interest and adaptors are ligated to the digested fragments. A single primer that is complementary of the adaptor sequence is used to amplify fragments of a desired size, for example, 400-800, 400-2000 bps, using PCR. Fragments that are outside the selected size range are not efficiently amplified. The processed target is then hybridized to nucleic acid arrays comprising SNP-containing fragments/probes. WGSA is disclosed in, for example, U.S. Patent Publication Nos. 20040185475, 20040157243 (also PCT Application published as WO04/044225), 20040146890, 20030186279, 20030186280, 20030232353, and 20040067493, and U.S. patent application Ser. Nos. 10/442,021 and 10/646,674, each of which is hereby incorporated by reference in its entirety for all purposes.

Given the millions of SNPs that are estimated to exist and the large subset already in databases, there is a need to prune this number down to a number that will fit on a few microarrays at current feature sizes. Applications of microarray for SNP genotyping have been described in e.g., a number of U.S. patents and patent applications, including U.S. Pat. Nos. 6,300,063, 6,361,947, 6,368,799 U.S. patent application Ser. No. 10/442,021 and US Patent Publication Nos. 20040067493, 20030232353, 20030186279, 20050260628, and 20030186280, all incorporated herein by reference in their entireties for all purposes. Methods and arrays for simultaneous genotyping of more than 10,000 and more than 100,000 SNPs have also been described for example in Kennedy et al. (2003) Nat. Biotech. 21:1233-7, Matsuzaki et al., (2004) Genome Res. 14(3): 414-425, and Matsuzaki et al (2004) Nature Methods, Vol 1, 109-111, all incorporated herein by reference in their entireties for all purposes.

The present invention also contemplates sample preparation methods in certain preferred embodiments. Prior to or concurrent with genotyping, the genomic sample may be amplified by a variety of mechanisms, some of which may employ PCR. See, e.g., *PCR Technology: Principles and Applications for DNA Amplification* (Ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (Eds. McPherson et al., IRL Press, Oxford); and U.S. Pat. Nos. 4,683,202, 4,683,195, 4,800,159 4,965,188, and 5,333,675, and each of which is incorporated herein by reference in their entireties for all purposes. The sample may be amplified on the array. See, for example, U.S. Pat. No. 6,300,070 which is incorporated herein by reference.

Other suitable amplification methods include the ligase chain reaction (LCR) (for example, Wu and Wallace, *Genomics* 4, 560 (1989), Landegren et al., *Science* 241, 1077 (1988) Alves and Carr *Nucleic Acid Res* 16:8723, (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA,* 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517, and 6,063,603, each of which is incorporated herein by reference). Other amplification methods that may be used are described in, U.S. Pat. Nos. 6,582,938, 5,242,794, 5,494,810, 4,988,617, each of which is incorporated herein by reference. Amplification may also be by multiple displacement amplification. For a description of multiple displacement assay, see for example Lasken and Egholm, *Trends Biotechnol.* 2003 21(12):531-5; Barker et al. *Genome Res.* 2004 May; 14(5):901-7; Dean et al. *Proc Natl Acad Sci* USA. 2002; 99(8):5261-6; and Paez, J. G., et al. *Nucleic Acids Res.* 2004; 32(9):e71. Multiplex PCR procedures are also disclosed in Shuber et al. Genome Res 5(5): 488-93 (1995), Brinson et al. Introduction to PCR/OLA/SCS, a multiplex DNA test, and its application to cystic fibrosis. Genet Test. 1997; 1(1):61-8, Additional methods of sample preparation and techniques for reducing the complexity of a nucleic sample are described in Dong et al., *Genome Research* 11, 1418 (2001), in U.S. Pat. Nos. 6,361,947, 6,391,592 and U.S. Patent Pub. Nos. 20030096235, 20030082543 and 20030036069.

In preferred embodiments large scale mapping of disease loci may be performed using a fixed panel of SNPs that interrogate the entire genome at a selected resolution. Arrays capable of interrogating fixed SNP panels are available from Affymetrix and include, for example, the Mapping 10K array, the Mapping 100K array set (includes 2 50K arrays) and the Mapping 500K array set (includes two ~250K arrays). These arrays and array sets interrogate more than 10,000, 100,000 and 500,000 different human SNPs, respectively. The perfect match probes on the array are perfectly complementary to one or the other allele of a biallelic SNP. Each SNP is interrogated by a probe set comprising 24 to 40 probes. The perfect match probes in a probe set are each different, varying in, for example, the SNP allele, the position of the SNP relative to the center of the probe and the strand targeted. The probes are present in perfect match-mismatch pairs. The SNPs interrogated by a mapping array or array set are spaced throughout the genome with approximately equal spacing, for example, the SNPs in the 10K array are separated by about 200,000 base pairs. The median physical distance between SNPs in the 500K array set is 2.5 kb and the average distance between SNPs is 5.8 kb. The mean and median distance between SNPs will vary depending on the density of SNPs interrogated. Methods for using mapping arrays see, for example, Kennedy et al., *Nat. Biotech.* 21:1233-1237 (2003), Matsuzaki et al., *Genome Res.* 14:414-425 (2004), Matsuzaki et al., *Nat. Meth.* 1:109-111 (2004) and U.S. Patent Pub. Nos. 20040146890 and 20050042654. Selected panels of SNPs can also be interrogated using a panel of locus specific probes in combination with a universal array as described in Hardenbol et al., *Genome Res.* 15:269-275 (2005) and in U.S. Pat. No. 6,858,412. Universal tag arrays and reagent kits for performing such locus specific genotyping using panels of custom molecular inversion probes (MIPs) are available from Affymetrix.

Computer implemented methods for determining genotype using data from mapping arrays are disclosed, for example, in Liu, et al., *Bioinformatics* 19:2397-2403 (2003), Rabbee and Speed, *Bioinformatics,* 22:7-12 (2006), and Di et al., *Bioinformatics* 21:1958-63 (2005). Computer implemented methods for linkage analysis using mapping array data are disclosed, for example, in Ruschendorf and Nurnberg, *Bioinformatics* 21:2123-5 (2005) and Leykin et al., *BMC Genet.* 6:7, (2005). Computer methods for analysis of genotyping data are also disclosed in U.S. Patent Pub. Nos. 20060229823, 20050009069, 20040138821, 20060024715, 20050250151 and 20030009292.

Methods for analyzing chromosomal copy number using mapping arrays are disclosed, for example, in Bignell et al., *Genome Res.* 14:287-95 (2004), Lieberfarb, et al., *Cancer Res.* 63:4781-4785 (2003), Zhao et al., *Cancer Res.* 64:3060-71 (2004), Nannya et al., *Cancer Res.* 65:6071-6079 (2005) and Ishikawa et al., *Biochem. and Biophys. Res. Comm.,* 333:1309-1314 (2005). Computer implemented methods for estimation of copy number based on hybridization intensity are disclosed in U.S. Patent Pub. Nos. 20040157243, 20050064476, 20050130217, 20060035258, 20060134674 and 20060194243.

In another embodiment target amplification by the disclosed methods is used for array-based sequencing applications. The sequence of a nucleic acid may be compared to a known reference sequence by hybridization to an array of probes that detects all possible single nucleotide variations in the reference sequence. Such arrays, known as resequencing arrays, are commercially available from Affymetrix, Inc. and have been described, for example, see Cutler, D. J. et al., *Genome Res.* 11(11), 1913-25, 2001. During sample preparation for resequencing analysis target sequences are amplified. Amplification may be, for example, by PCR amplification using pairs of primers that are specific for segments of the target to be analyzed. Long range PCR may be used. Strand displacing amplification methods may also be used, for example, the target may be amplified by long range amplification using a strand displacing enzyme such as Phi 29 or Bst DNA polymerase. Resequencing arrays may be used to analyze both strands of 30 kb or more and 300 kb or more to detect polymorphisms in the sample sequence compared to a reference sequence.

Other suitable amplification methods include the ligase chain reaction (LCR) (for example, Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA,* 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517, and 6,063,603, each of which is incorporated herein by reference). Other amplification methods that may be used are described in U.S. Pat. Nos. 6,852,938, 5,242,794, 5,494,810, and 4,988,617 each of which is incorporated herein by reference.

Additional methods of sample preparation and techniques for reducing the complexity of a nucleic sample are described in Dong et al., *Genome Research* 11, 1418 (2001), in U.S. Pat. Nos. 6,361,947, 6,391,592 and 6,872,529 and U.S. Patent Publication Nos. 20030036069, 20030096235 and 20030082543. Additional methods of using a genotyping array are disclosed, for example, in U.S. patent application Ser. No. 10/442,021, and U.S. Patent Publication Nos. 20040146883, 20030186280, 20030186279, 20040067493, 20030232353, 20060292597, 20050233354, 20050074799 and 20040185475.

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* ($2^{nd}$ Ed. Cold Spring Harbor, N.Y., 1989); Berger and Kimmel *Methods in Enzymology,* Vol. 152, *Guide to Molecular Cloning Techniques* (Academic Press, Inc., San Diego, Calif., 1987); Young and Davis, *P.N.A.S,* 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference The present invention also contemplates signal detection of hybridization between ligands in certain preferred embodiments. See U.S. Pat. Nos. 5,143,854, 5,578,832, 5,631,734, 5,834,758, 5,936,324, 5,981,956, 6,025,601, 6,141,096, 6,185,030, 6,201,639, 6,218,803, and 6,225,625 in U.S. Patent Pub. No. 20040012676 and in PCT Application PCT/

US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758, 5,856,092, 5,902,723, 5,936,324, 5,981,956, 6,025,601, 6,090,555, 6,141,096, 6,185,030, 6,201,639; 6,218,803; and 6,225,625, in U.S. Patent Pub. Nos. 20040012676 and 20050059062 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes, etc. The computer-executable instructions may be written in a suitable computer language or combination of several languages. Basic computational biology methods are described in, for example, Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have preferred embodiments that include methods for providing genetic information over networks such as the Internet as shown in U.S. Patent Pub. Nos. 20030097222, 20020183936, 20030100995, 20030120432, 20040002818, 20040126840, and 20040049354.

b) Definitions

The term "array" as used herein refers to an intentionally created collection of molecules which can be prepared either synthetically or biosynthetically. The molecules in the array can be identical or different from each other. The array can assume a variety of formats, for example, libraries of soluble molecules; libraries of compounds tethered to resin beads, silica chips, or other solid supports.

The term "complementary" as used herein refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

The term "hybridization" as used herein refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see, for example, Sambrook, Fritsche and Maniatis. "Molecular Cloning A laboratory Manual" $2^{nd}$ Ed. Cold Spring Harbor Press (1989) which is hereby incorporated by reference in its entirety for all purposes above.

The term "hybridization conditions" as used herein will typically include salt concentrations of less than about 1M, more usually less than about 500 mM and preferably less than about 200 mM. Hybridization temperatures can be as low as 5° C., but are typically greater than 22° C., more typically greater than about 30° C., and preferably in excess of about 37° C. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone.

The term "hybridization probes" as used herein are oligonucleotides capable of binding in a base-specific manner to a complementary strand of nucleic acid. Such probes include peptide nucleic acids, as described in Nielsen et al., Science 254, 1497-1500 (1991), and other nucleic acid analogs and nucleic acid mimetics.

The term "hybridizing specifically to" as used herein refers to the binding, duplexing, or hybridizing of a molecule only to a particular nucleotide sequence or sequences under stringent conditions when that sequence is present in a complex mixture (for example, total cellular) DNA or RNA.

The term "label" as used herein refers to a luminescent label, a light scattering label or a radioactive label. Fluorescent labels include, inter alia, the commercially available fluorescein phosphoramidites such as Fluoreprime (Pharmacia), Fluoredite (Millipore) and FAM (ABI). See U.S. Pat. No. 6,287,778.

The term "oligonucleotide" or sometimes refer by "polynucleotide" as used herein refers to a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term "solid support", "support", and "substrate" as used herein are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

Multiplex Target Amplification Methods

In a first aspect, the methods disclosed herein provide a simple, multiplex targeted amplification method that does not require PCR. For each target to be amplified a circularization probe is synthesized containing sequences that are complementary to sequences that flank the target to be amplified. In particular, the circularization probe includes a first region that is complementary to a first sequence at the 5' end of the target and a second region that is complementary to a second sequence at the 3' end of the target, both regions of the probe being complementary to the same strand of the target. The circularization probe is designed so that when the target strand is hybridized to the circularization probe the 5' and 3' flanking sequences are brought together to facilitate joining of the ends of the strand to form a circularized target strand. The circularized target strand includes the 5' and 3' flanking sequences and the target.

In some embodiments the circularization probe hybridizes to the target so that flaps of non-target sequence are generated. The flaps can be 5' or 3' overhangs. The flaps can be removed by enzymatic activity to generate target ends for ligation to form circular target strands.

After circularization of the targets to be amplified, non circularized nucleic acids in the mixture can be digested using exonuclease activities and the circles can be amplified using rolling circle amplification (RCA). Primers for the RCA may be, for example, random primers, target specific primers, the circularization probes or fragments of the circularization probes. For a description of rolling circle amplification see, for example, U.S. Pat. Nos. 6,183,960 and 6,210,884 to Lizardi and U.S. Pat. No. 6,593,086 to Zhang. See also, Fire and Xu, "Rolling replication of short DNA circles", Proc. Natl. Acad. Sci. USA 92:4641-4645 (1995), Zhang, D Y, et al. Amplification of target-specific ligation-dependent circular probe. Gene, 211(2): 277-285, 1998 and Lizardi, P M, et al., Mutation Detection and Single-Molecule Counting Using Isothermal Rolling-Circle Amplification, Nature Genetics, 19: 225-232, 1998. See also Kumar U.S. Pat. No. 5,912,124.

The presently disclosed methods are similar to those disclosed in Dahl et al. Nucleic Acids Res 33:e71 (2005) in that two sequence specific regions from the same strand of targeted DNA sequence separated by some distance are used to facilitate formation of a single stranded circle from the target. However, in the method taught by Dahl et al., the method incorporates universal priming sites into the circularized target and the subsequent amplification is by PCR using primers to the universal priming sites. The method of Dahl et al. therefore requires the use of two oligonucleotides for each target, referred to as the "vector oligonucleotide" and the "selector probe". The vector oligonucleotide is about 34 bases in length and contains the universal priming sites while the selector probe is longer (~70 bases) and contains the complement of the vector oligonucleotide flanked by target specific ends. The presently disclosed methods require a single oligonucleotide similar to the selector probe but lacking the region that is the complement of the vector oligonucleotide. The presently disclosed methods therefore require one oligonucleotide per target instead of the two oligonucleotides required by the previous methods and the target specific oligonucleotide is shorter (~40 instead of ~70 bases) because no universal priming sites are required. Porreca et al. Nat Methods 4(11):931-6 (2007) also describes a method for multiplex amplification of a selected set of target sequences based on the padlock probe methodology described in, for example, U.S. Pat. No. 5,871,921 (Landegren et al.)., Hardenbol et al. Nat. Biotechnol. 21, 673-678 (2003) and Hardenbol et al. Genome Res. 15, 269-275 (2005).

In the presently disclosed methods a single oligonucleotide of about 40 bases may be used for each target to be amplified. In some embodiments the oligonucleotide may be shorter or longer, for example, 12 to 100 bases. Because the target regions of the circularization probe are juxtaposed and not separated by universal priming sites the sequences can be selected to facilitate the use of a 5' flap endonuclease, allowing the use of randomly sheared or fragmented genomic DNA. The ends of the fragments of the input nucleic acid need not be known.

In one embodiment the 5' and 3' target flanking regions are selected so that they include common sequences of about 2 to 8 bases at the 5' end of the 5' target flanking region and at the 3' end of the 3' target flanking region. After ligation, the targeted DNA is circularized, and the uncircularized DNA, probes, and other nucleic acid with free ends may be removed by treatment with specific exonucleases, such as exonuclease I, exonuclease VII, exonuclease III and T7 exonuclease. The circled DNAs are then amplified equally with random primers using DNA polymerase of high strand displacement such as Phi29. Commercial available kits such as TempliPhi from GE Healthcare can be used. Alternatively, the same probe pool can be used with Phi29 to produce the products. These multiplex amplified products can be used directly in many applications, especially resequencing by tiling array or genotyping.

A method of simple multiplex targeted amplification of genomic DNA, cDNA or RNA is described herein. In general there are four different approaches contemplated: (1) using DNA targets that have perfect ends by cleaving the DNA with one or more restriction enzymes and designing the probes accordingly; (2) using targets that have a 5' flap and a single base 3' flap generated by cutting the DNA with one or more restriction enzymes and designing the probes accordingly; (3) targeting the probe to hybridize so that the 5' end is perfectly complementary to the probe and the 3' end hybridizes to generate a 3' flap using DNA cut with one or more restriction enzymes; and (4) targeting the probe to hybridize to two regions flanking a region of interest and resulting in double flaps using random sheared DNA (though restriction enzyme cut DNA can be used also).

A splint oligonucleotide or circularization probe is synthesized containing two regions (T1' and T2' in FIG. 1) with length ranging preferably from 6 to 60 bases and complementary to regions T1 and T2, respectively, of the genomic DNA or cDNA of the target species of interest. T1 and T2 are separated by a region that will be amplified. This region may be, for example, 50 to 500 bases or 500 to 5,000 bases or more than 5,000 bases). In preferred aspects the circularization probe length is about 40 bases (including ~20 bases for each of T1 and T2). This length of oligo can be synthesized easily with high quality even without purification. A pool of these circularization probes targeting different regions of the DNA can be used to hybridize to the desired targeted DNA, allowing the formation of circularized DNA after ligation (FIG. 1).

In FIG. 1 each of four different approaches are shown (A.-D.) In each, the DNA input is [101] and the circularization probe is [103]. In the embodiment shown in FIG. 1A the probe 103 hybridizes to the DNA 101 so that the ends of the DNA are separated by at least a nick. The probe has a 5' region T1' that is complementary to the 5' end of the target 101 and a 3' region T2' that is complementary to the 3' end of the target. The ends of the target are known so the circularization probe is designed accordingly. T1' and T2' hybridize to the target so that the ends of the target are juxtaposed. The nick can be closed by a ligation step 105 to generate a closed circular DNA target 107. The closed circular DNA target can then be amplified by RCA. In some aspects there may be a gap between T1 and T2 upon hybridization of the circularization probe and the gap may be filed by a DNA polymerase.

In FIG. 1B the DNA 101 hybridizes to the probe 103 so that there is a 5' flap of two or more bases 109 and a 3' flap of a single base 111. The structure is recognized by 5' flap nucleases which catalyze removal of the 5' flap and ligation of the end of the 3' flap to the new 5' end of the target strand generated by cleavage by the 5' flap nuclease. The resulting nick can be closed by ligation and the resulting circles amplified.

In FIG. 1C the DNA 101 hybridizes to the probe 103 to generate a 3' flap of two or more bases. The 5' end of the target is of known sequence and the 5' end of the circularization probe is designed to be complementary to the known 5' end of the target. The 3' end of the circularization probe is complementary to a region that is within the target. It is not necessary to know the location of the 3' end of the fragment. A 3' flap nuclease is used to remove the 3' flap. A DNA polymerase may be used to extend the 3' end generated by the 3' flap nuclease to create a gap to be closed by ligase. The resulting circles can be amplified.

In FIG. 1D the DNA 101 hybridizes to the probe 103 to generate a 5' flap of two or more bases 109 and a 3' flap of two or more bases 119. The 5' flap nuclease removes the 5' flap and a 3' to 5' exonuclease activity is used to remove the 3' flap. A ligase is used to join the juxtaposed ends of the target that result. The circularized targets can be amplified.

For the embodiments shown in FIG. 1A both ends of the target are defined by restriction sites and the probe is designed to hybridize to be complementary to regions flanking selected restriction sites. Because there is an optimal size range for the circle to be efficiently amplified the choice of restriction enzymes may limit the targets that are available for efficient amplification in a single reaction. To be efficiently amplified, target regions are selected to be flanked by selected restriction enzyme sites separated by a distance that is within the length that can be efficiently amplified. Preferably the target fragments are a defined distance from the restriction sites both upstream and downstream. For the embodiments shown in FIGS. 1B and C only one end of the probe needs to be defined by a restriction site and the second end can be selected for optimal circle size.

In a first embodiment, shown in FIG. 1A, the circularization probes may be designed based on the restriction digestion so that once hybridized, a perfect nick will be formed (the 5' and 3' ends of the target will be juxtaposed) and the nick can be sealed (in step 113) by formation of a phosphodiester bond (105) by DNA ligase, for example, T4 DNA ligase or Taq DNA ligase. After exonuclease treatment, the circularized DNAs 107 can be amplified by rolling cycle amplification (RCA). In one aspect, the probe 103 may be used as a primer for RCA. Alternatively, random primers, a portion of the circularization probe or a target specific sequence outside of the region complementary to the circularization probe may be used as primers.

In another embodiment, shown in FIG. 1B, the circularization probes are designed so that when hybridized to the target a structure is generated that has a nick, a 5' flap 109 and a 3' flap of a single base 111. A structure-specific flap nuclease may be used to remove the 5' flap, for example, the 5' to 3' exonuclease/endonuclease domain of the E coli DNA polymerase, Taq DNA polymerase or other eubacterial DNA polymerase, or the Archeal or eukaryotic flap endonuclease 1 (FEN1), including human FEN1 and Pfu FEN1. In a preferred embodiment, the circularization probe may be designed so that the 3' end base of the 5' flap is the same base as the base of the 3' flap. In step 115, a 5' flap nuclease is used to remove the 5' flap (109) and a ligase is added to ligate the ends of the target to form a circular target. The structure shown in the left hand side of FIG. 1B may be referred to as a 5' flap with 1 base 3' flap.

In another embodiment, the probe hybridizes to the target so that the resulting structure has a 3' flap 119 and no flap at the 5' end, as shown in FIG. 1C, a 3' flap nuclease may be used, such as the human *Xeroderma pigmentosa* complementation group F (XPF) (Sijbers A M et al., Cell 86: 811-822, 1996), Archeal *P. furiosus* helicase-associated endonuclease (Hef) (Komori et al., Genes Genet. Syst. 77: 227-241, 2002), Archeal *S. solfataricus* XPF (Roberts J A et al., Mol. Microbiol. 48: 361-371, 2003) and Nar71 (Guy C P et al., Nucleic Acids Research 32: 6176-6186, 2004). See also, Matsui et al., J Biol Chem 274:18297-18309 (1999) for a description of FEN1 in *Pyrococcus horikoshii*. The 3' flap nucleases generally cuts a few sites near the flap junction (generating a gap) and DNA polymerase may be used in step 121 to fill in the gap for ligation of the ends. In a preferred aspect, less than all four dNTPs may be included in the reaction, for example, only dATP and dGTP may be included and the probes are designed with a gap of only dA or dG after 3' flap nuclease treatment.

Figure 2:
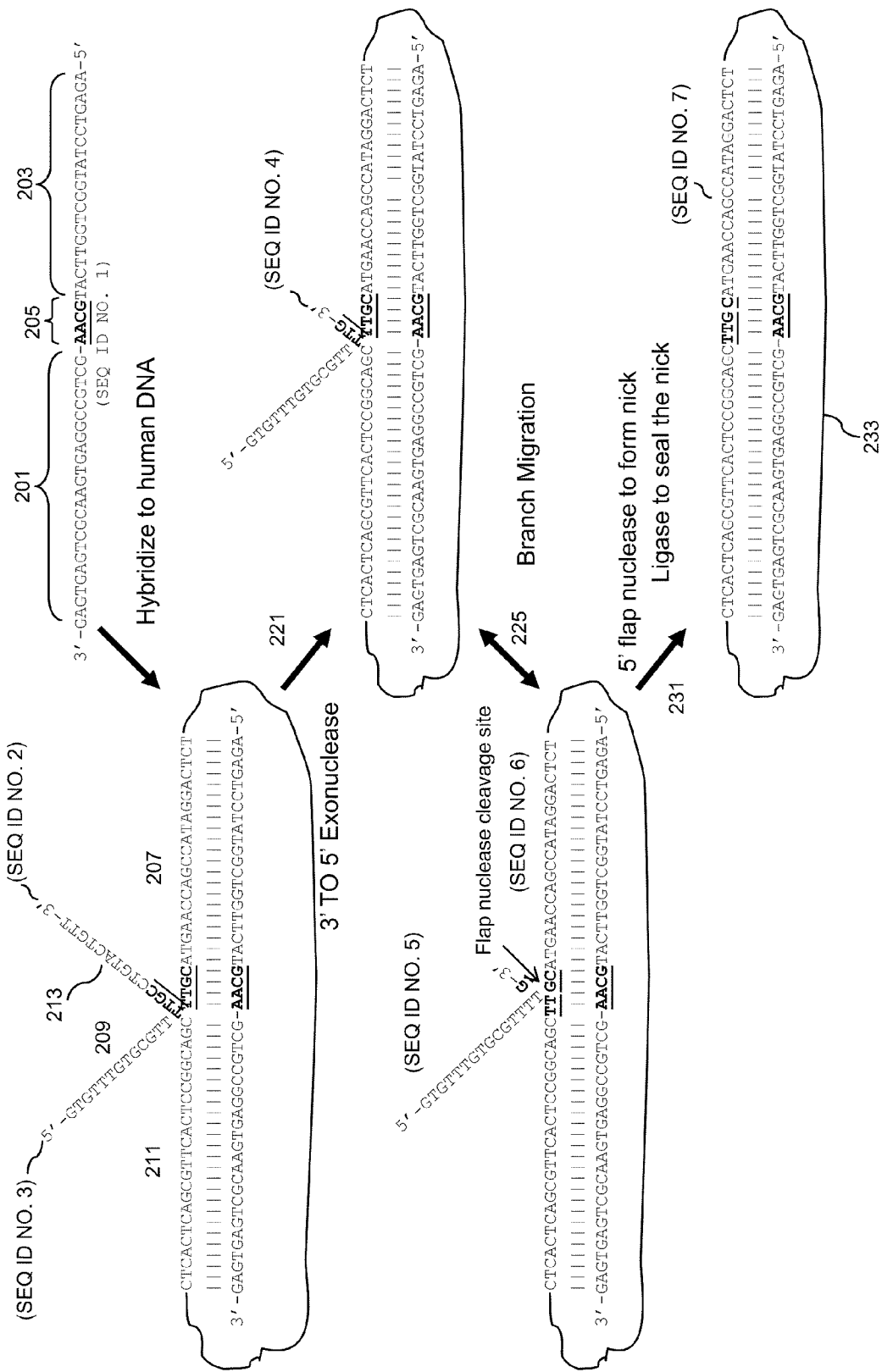
FIG. 2 shows an example of removal of double flaps for ligation. The example is the human integrin alpha 6 gene (ITGA6) exon 2.

In the most flexible embodiment (shown in FIG. 1D), random sheared DNA, fragmented, for example, mechanically, chemically or enzymatically using an enzyme such as DNase or Apyrase, may be hybridized to the probes to generate primarily double flap structures as shown in FIG. 1D and also in FIG. 2. The random fragmentation will also generate some nick or gapped structures. The T1 and T2 sequences can be selected to flank the sequence of interest and preferably to have a common sequence at the 3' end of T2 and at the 5' end of T1. It has been observed that cleavage by yeast FEN1 was more efficient at cleavage when the upstream primer contained a 1-nucleotide 3'-tail than when the upstream primer was fully annealed (both contained a 5' tail). See, Kao H-I et al., J. Biol. Chem. 277: 14379-14389, 2002. Since 3' flap nucleases can generate a gap and can also cut nicking products, the preferred enzyme for step 123 is a 5' flap nuclease. A 3' to 5' exonuclease is also added to cleave the 3' flap and a ligase is used to close the nick. To allow the cleavage of 5' flap nuclease of the double flap structure the circularization probe is designed so that the two specific target regions (T1 and T2) are selected so the 3'-end sequence of one target region will overlap with the 5'-end sequence of the other target region to create 2 to 8 bases of identical sequence. This shared sequence is present only once in the probe but is present in each of the target sequences.

In the double flap example shown in FIG. 2 the overlapping region is the "TTGC" present in both SEQ ID NO. 2 and 3 and underlined. The probe (SEQ ID NO. 1) has the AACG complement, but only once. Second, single stranded DNA-specific exonucleases such as exonuclease I, exonuclease T or exonuclease VII may be added together with 5' flap nucleases (e.g., human FEN1). The 3' to 5' ssDNA exonucleases will degrade the ssDNA 3' flap, but most likely with some blunts, some 3' extension of a few bases or even a few bases into the dsDNA. Therefore, with the few overlapping bases, the creation of 5' flap with 1 base of 3' flap is significantly increased in the presence of 3' to 5' exonucleases, allowing removal of 5' flap to create a perfect nick with high specificity and efficiency (FIG. 2). The nick may be ligated in the presence of DNA ligase. In a preferred embodiment, a computer program may be used to select the T1 and T2 sequences so that they have overlapping end sequences.

As shown in FIG. 2, the probe, 5'-AGAGTCCTAT GGCTGGTTCA TGCAAGCTGC CGGAGTGAAC GCTGAGTGAG-3' (SEQ ID NO. 1), has a 5' targeting region 203 and a 3' targeting region 201 and a shared region 205. The 5' targeting region 203 is complementary to a first region 207 in the target and when hybridized to the target 5' overhang 209 is results. The 3' targeting region 201 is complementary to a second region 211 in the target and when hybridized to the target 3' overhang 213 results.

In step 221 a 3' to 5' exonuclease is added and overhang 213 is digested so that only a short flap remains (TTG is shown). The flap is complementary to the shared region 205 of the probe.

The complementarity of the 3' end of SEQ ID No. 4 to the shared region of the probe allows reversible branch migration in step 225 so that only a single base at the 3' end of SEQ ID No. 4 is unpaired (shown as a G base). In step 231, the flap nuclease cleaves between the G and C at positions 16 and 17 of SEQ ID No. 3, cleaving SEQ ID No. 3 into two fragments 5'-GTGTTTGTGC GTTTTG-3' (SEQ ID No. 5) and 5'-CATGAACCAG CCATAGGACT CT-3' (SEQ ID No. 6), and leaving a nick (between the G at the 3' end of SEQ ID No. 4 and the C at the newly generated 5' end of SEQ ID No. 5. The nick can be closed by ligase. The resulting product 233 is a close circular target 233 containing SEQ ID NO. 7.

The sequences shown in FIG. 2 are the exemplary products expected. SEQ ID No. 1 (5'-AGAGTCCTAT GGCTGGTTCA TGCAAGCTGC CGGAGTGAAC GCTGAGTGAG-3') is the circularization probe for this target. SEQ ID No. 2 (5'-CTCACTCAGC GTTCACTCCG GCAGCTTGCC TGTACTGTT-3') is the sequence at the 5' end of the target with the 5' portion being complementary to the 3' portion of SEQ ID No. 1 and the 3' portion forming a 3' flap. SEQ ID NO. 3 (5'-GTGTTTGTGC GTTTTGCATG AACCAGCCAT AGGACTCT-3') is the sequence at the 3' end of the target with the 5' portion forming a 5' flap and the 3' portion being complementary to the 5' portion of SEQ ID No. 1. SEQ ID NO. 4 (5'-CTCACTCAGC GTTCACTCCG GCAGCTTG-3') is generated from SEQ ID No. 2 after 3' to 5' exonuclease treatment. SEQ ID No. 5 (5'-GTGTTTGTGC GTTTTG-3') is the 5' portion of SEQ ID No. 3 after cleavage with flap nuclease and SEQ ID No. 6 (5'-CATGAACCAG CCATAGGACT CT-3') is the 3' portion of SEQ ID No. 3 after cleavage with flap nuclease. SEQ ID No. 7 (5'-<u>CTCACTCAGCGTTCACTCCGCAGCTTGCAT</u> GAACCAGCCA TAGGACTCT-3') is the 3' and 5' target flanking regions after ligation and includes the 5' portion of SEQ ID No. 2 and the 3' portion of SEQ ID No. 3. The underlined section originated is from SEQ ID No. 2 and the bold section is from SEQ ID No. 3.

In on embodiment where a 5' flap endonuclease is used a 5' to 3' ssDNA exonuclease, such as RecJ or Exo VII, may be used to shorten the length of 5' flap. By doing this, the efficiency of the removal of long 5' flaps, for example, greater than 50 bases, may be increased. Removal efficiency has been shown to decrease with increased flap length, although very good cleavage can be obtained up to 500 bases in most cases. The lengths of the flaps may be, for example, 1 to 500 bases or 1 to 1,000 bases. The length of the targets to be amplified may be about 100 to 5,000 bases, or about 100 to 10,000 bases. In some aspects each target may be greater than 10,000 bases. Because RCA is being used for amplification and not PCR the length of the amplicons may be longer. In some aspects that circularization probe may be selected to include a recognition site for a restriction endonuclease. After RCA the endonuclease may be used to cleave the RCA product into segments.

In another aspect Dna2 may be used to shorten the 5' and 3' flaps. See Kim et al., *Nucleic Acids Res.* 34:1854-1864 (2006) and Stewart et al. JBC 281:38565-38572 (2006).

Once the targeted DNA is circularized by ligation, the DNAs other than the circled single stranded DNA may be removed by treatment with exonucleases, for example, exonuclease I, exonuclease VII, exonuclease III and T7 exonuclease.

In preferred aspects, the circularized product is amplified with minimal bias using Phi29 and random primers. Alternatively, the starting probe pool can be used with Phi29 to produce the products. These multiplex amplified products can be used directly in many applications, especially resequencing by tiling array or genotyping.

1. In one aspect, the targets may be used for resequencing using the Affymetrix resequencing arrays, for example, the CUSTOMSEQ array product. Resequencing arrays allow variation detection in a sequence of interest by tiling probes for all possible single nucleotide variations within the sequence. They have been used in a number of studies. See, for example, Cutler et al., Genome Res. 11:1913-25 (2001), Lipkin et al., Nature Genet. 36:694-699 (2004), Zwick et al., Genome Biol 6:R10, (2005) and Warrington et al., Hum Mutat 19:402-9 (2002). Resequencing arrays are currently commercially available for analysis of up to 300 kb of double stranded DNA (600,000 bases total). Arrays can be purchased for 50 kb or 100 kb as well. Larger sequences can also be analyzed. The amplification methods disclosed herein can be used in place of the long range PCR amplification methods currently used for resequencing, eliminating the need to normalize and pool amplicons prior to hybridization. In some aspects kits for amplification to prepare targets for resequencing are disclosed. Preferred kits may have one or more of the following: at least 100 different dU probes, including one for each target to be amplified, a ligase, UDG and a flap endonuclease, that may be selected from a 5' flap endonuclease and a 3' flap endonuclease. The amplification products may be fragmented and labeled by standard methods prior to hybridization to arrays. Fragmentation may be, for example, by DNase treatment with end labeling using terminal transferase.

The non-PCR targeted multiplex amplification methods disclosed herein are simple and highly specific. The embodiments shown in FIGS. 1A and B are preferably used with targets that have known and defined ends, for example, restriction fragments. As a result this method may be limited somewhat in the choice of the targets that can be amplified because they require at least one defined end (defined 5' and 3' ends in 1A and defined 3' ends in 1B). Defined ends may be achieved, for example, by cleavage with one or more restriction enzymes. Although the requirement for defined ends may make it difficult to amplify some targets using this approach, resulting in less than 100% coverage of a genome, choice of enzymes may facilitate amplification of a majority of the targets of interest. Use of multiple enzymes may be used to further increase the coverage of these embodiments.

The embodiment shown in FIG. 1C uses a 3' flap nuclease to remove the 3' flap. The circularization probes are designed to be complementary to a region at the 5' end of the target and to include the 5' end generated by the fragmentation method, for example, if fragmentation is by restriction digestion then the T1' portion of the circularization probe is complementary to the region at the end of the restriction fragment and generated by cleavage. The T2' portion is not restricted to the natural fragment end and can be selected to generate a desired circle length. Preferably the 3' flap is less than about 500 bases and more preferably less than about 50 bases.

The double flap strategy shown in FIG. 1D is the most flexible embodiment because it does not require specific ends to be generated in the target by the initial cleavage so there are fewer limitations on the cleavage methods and the coverage can be 100%, similar to individual PCR. Optimization of the choice of flap nucleases and exonucleases and reaction conditions may be used to overcome the reduced efficiency that is expected when removal of flaps at both ends is required.

In many aspects of the presently described methods a flap endonuclease is used to remove overhanging ends prior to ligation of the ends of the target DNA. Flap endonucleoases (FEN-1) have been described in a number of organisms including mouse, human, yeast and a number of thermophilic organisms. They are structure-specific endonucleases that cleave 5' flap structures endonucleotyltically and have a double-strand-specific 5'-3' exonuclease activity. The exonuclease activity utilizes double-stranded DNA with a nick or gap, and the endonuclease activity requires a flap structure. In prokaryotes the FEN 1 activity is the 5' nuclease domain of DNA polymerase I. There is a separate polypeptide in eukaryotes, archaea and some bacteriophage. For additional information about different enzymes and substrate specificities, see, Xu et al., *J. Biol. Chem.* 276:30167-30177 (2001) and Kaiser et al. J Biol Chem 274:21387-21394 (1999). FENs catalyze hydrolytic cleavage of the phosphodiester bond at the junction of single and double stranded DNA (see, Harrington and Lieber, EMBO 13:1235-46 (1994); Harrington and Lieber, J Biol Chem 270:4503-8 (1995)). In cells, FEN-1 is one of the enzymes required for lagging strand DNA replication and in particular, the maturation of Okazaki fragments by generation of ligatable nicks. Flap endonuclease activities are used, for example, in the TAQMAN assay and in the INVADER assay. Taq DNA polymerase I endonucleolytically cleaves DNA substrates, releasing unpaired 5' arms of bifurcated duplexes. See Lyamichev et al., PNAS 96:9143 (1999) and Lyamichev et al., *Science* 260: 778-783 (1993).

Targets amplified using the methods disclosed herein may be used for a variety of studies. In one aspect the targets contain known polymorphic regions and the amplified targets are analyzed to determine the genotype of the sample at the polymorphic regions. In another aspect the methods are combined with methods for analysis of methylation, for example, the targets may be treated with bisulfite prior to amplification so that methylation dependent modifications are made to the sequence and those changes are maintained in the amplification product and can be detected as changes in the sequence. Methylation detection using bisulfite modification and target specific PCR have been disclosed, for example, in U.S. Pat. Nos. 5,786,146, 6,200,756, 6,143,504, 6,265,171, 6,251,594, 6,331,393, and 6,596,493.

Prior to circularization, the nucleic acid sample containing the targets may be treated with bisulfite. During bisulfite treatment, unmethylated cytosine is converted to uracil and methylated cytosine remains cytosine. See Clark et al., Nucleic Acids Res., 22(15):2990-7 (1994). When the modified strand is copied a G will be incorporated in the interrogation position (opposite the C being interrogated) if the C was methylated and an A will be incorporated in the interrogation position if the C was unmethylated. This results in a detectable sequence difference between methylated and unmethylated positions.

Kits for DNA bisulfite modification are commercially available from, for example, Human Genetic Signatures' Methyleasy and Chemicon's CpGenome Modification Kit. See also, WO04096825A1, which describes bisulfite modification methods and Olek et al. Nuc. Acids Res. 24:5064-6 (1994), which discloses methods of performing bisulfite treatment and subsequent amplification on material embedded in agarose beads. In one aspect a catalyst such as diethylenetriamine may be used in conjunction with bisulfite treatment, see Komiyama and Oshima, *Tetrahedron Letters* 35:8185-8188 (1994). See also, Hayatsu et al, *Proc. Jpn. Acad. Ser. B* 80:189-194 (2004) for alternative procedures.

Bisulfite treatment allows the methylation status of cytosines to be detected by a variety of methods. For example, any method that may be used to detect a SNP may be used, for examples, see Syvanen, Nature Rev. Gen. 2:930-942 (2001). Methods such as single base extension (SBE) may be used or hybridization of sequence specific probes similar to allele specific hybridization methods. In another aspect the Molecular Inversion Probe (MIP) assay may be used. The MIP assay is described in Hardenbol et al., *Genome Res.* 15:269-275 (2005) and in U.S. Pat. No. 6,858,412.

The methods may also be used for analysis of copy number. See, for example Wang et al., *Nucleic Acids Res.* 33:e183 (2005) and Ji et al., *Cancer Res.* 66:7910-9 (2006). In other aspects the methods may be used to analyze targets from compromised samples, for example, formaldehyde fixed and paraffin embedded (FFPE) samples or degraded samples. In many embodiments the amplification products may be analyzed by hybridization to an array of probes. Preferred arrays include those commercially available from Affymetrix, Inc. and include tiling arrays, gene expression arrays, mapping arrays (10K, 100K, 500K, and SNP 5.0), promoter arrays and tag arrays. The amplification products may also be analyzed by hybridization to arrays of oligonucleotides attached to beads or other solid supports.

Figure 3:
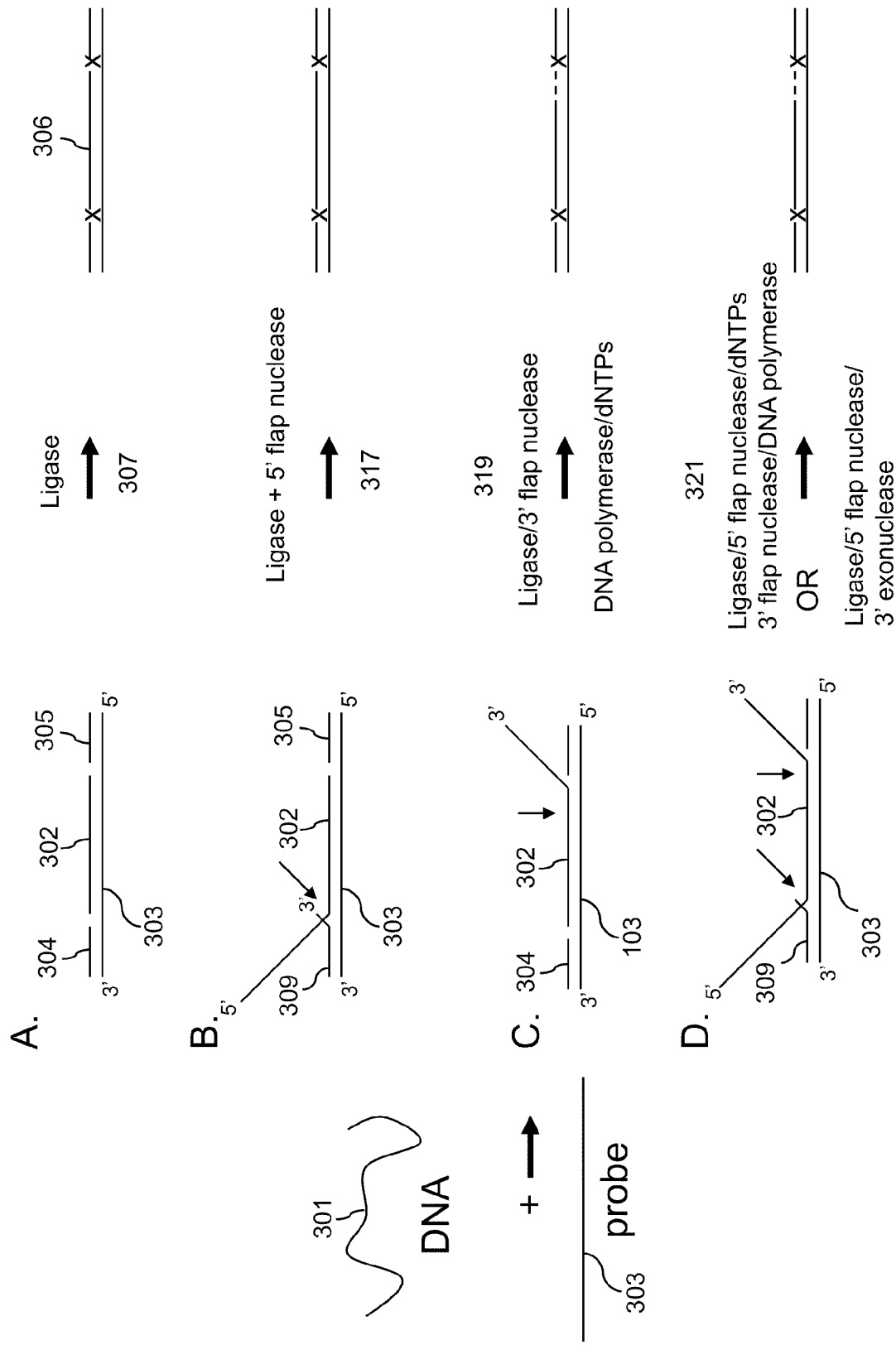
FIG. 3 shows a schematic of four different embodiments of a multiplex amplification method.

In another aspect methods for multiplex target amplification using flap nucleases to generate specific ends for ligation of common priming sequences are disclosed. These methods are illustrated in FIG. 3 and are related to methods for probe-based multiplex PCR with common oligo addition that have been previously described in U.S. Pat. No. 7,208,295 and Faham M et al., *PNAS* 102: 14717-14722, (2005), each of which is incorporated herein by reference in its entirety for all purposes. In these methods pools of probes are used to capture and normalize the targeted DNAs followed by the ligation of common oligos to the targets. The common oligos flank the targets and allow multiplex amplification of the targets using common primers to the common oligo sequences. In preferred aspects, the probes contain dU replacing at least some of the dT, allowing removal of the probes by treatment with UDG to generate abasic sites and cleavage at the abasic sites before amplification of the targets. The dU-containing probes can be synthesized chemically, but in preferred embodiments they are obtained by PCR amplification using specific primers and replacing dTTP with dUTP The use of dU probes in 2-step multiplex PCR has been previously described in Faham M et al., *PNAS* 102: 14717-14722, (2005), but briefly, the method is as follows. In the first stage, multiple pairs of oligos (from 50-200 pairs) are added in the same tube and PCR is performed. Then different pools of 50 to 200-plex first stage products are pooled and used for capture or normalization with common oligos and ligase, followed by a second PCR with common primers. The second stage can be in a plex of about 1000 but can be over 10,000 ("plex" herein refers to the number of targets amplified in a single reaction, so 100 plex means that about 100 different targets are amplified in the reaction). The first stage PCR is with specific target primers for each target so the number of amplifications that can be done in a single reaction (the plex level) is currently most efficient at lower levels, for example, less than 200, preferably less than 100 or less than 50.

In many embodiments, the dU probe includes a target specific region flanked by common regions at both ends. The dU probes may be obtained, for example, by PCR with the inclusion of dUTP. The dUTP may replace the dTTP in the reaction or the reaction may include varying amounts of both dUTP and dTTP. Individual dU probes are obtained and pooled together, preferentially in equal or approximately equal molar concentration. This pool is then used in a capture reaction with genomic DNA or cDNA, together with two common oligonucleotides (C1 and C2) that are complementary to the common sequences in one strand of the dU probe. After ligation the strand that is formed has the structure C1-target-C2 and can be amplified with primers designed to target the C1 and C2 regions.

In some aspects, a unique tag sequence can be also included in a dU probe. When a tag is included an oligonucleotide complementary to the tag may also be included. The probe may be designed so that the tag complement is included in the ligated product along with the target and flanked by the common oligonucleotides. See U.S. Pat. No. 7,208,295 for a discussion of how tag sequences may be included in dU probes and how they may be used in subsequent detection methods. When the C1-tag complement-target-C2 is amplified the tag complement is amplified as well.

The dU method does not require 2 stages of PCR and can be performed using targeted genomic DNA or cDNA. It has been demonstrated to have a sensitivity equivalent to or lower than 60 ng human genomic DNA (30 zmol). In some aspects nucleases, such as single strand specific nucleases or mung bean nuclease, may be used to cleave flaps created during the hybridization of targeted DNA to the dU probes. The examples included herein demonstrate methods for successful multiplex PCR amplification using genomic DNA directly.

In FIG. 3 each of four different four embodiments is shown (A-D). In each, the DNA input 301 contains the target 302 that contains a region that is complementary to the dU probe 303 for that target. Each has an enzymatic step (307, 317, 319 and 321) that includes ligation. The product generated (shown to the right of horizontal arrows) is double stranded and includes a top strand (306) that includes flanking oligonucleotides ligated to a target (junctions where ligation has closed a nick are shown by an X) and the input probe (303). The probe can then be separated from 306 and 306 can be amplified by PCR using primers to the common flanking sequences. The probe 303 may, for example, contain deoxyuracil and can be fragmented by using UDG or UNG in combination with heat treatment or enzymatic cleavage with an endonuclease that recognizes abasic sites generated by UDG.

In the first embodiment, shown in FIG. 3A, the ends of the DNA are "perfect" used herein to indicate that the ends of the target 302 are known and defined, for example, by cleavage with one or more restriction enzymes or by amplification with target specific primers. The dU probe 303 is designed so that the target 302 hybridizes to the probe so that there are no unpaired bases in the target. The oligonucleotides 304 and 105 that are complementary to the common sequences at the ends of the dU probe hybridize to the dU probe flanking the target so that the ends are adjacent, leaving a "nick" that can be closed by ligase in step 307. This embodiment may be referred to as the "nick" embodiment. Ligation between the 5' end of 302 and the 3' end of 304 and between the 3' end of 302 and the 5' end of 305 results in the single strand 306 that includes the target flanked by the common sequences 304 and 305. The dU probe 303 may then be digested using UDG cleavage methods and 306 can be amplified by PCR using common primers.

In another embodiment, shown in FIG. 3B ("5' flap with 1 base 3' flap") the dU probes may be designed to hybridize to targets so that one end of the target 302 forms a single stranded 5' flap when the target is hybridized to the dU probe. Similarly, in the embodiment shown in FIG. 3C the target hybridizes to the probe so that a 3' flap is formed. For the embodiments shown in FIGS. 3B and C the genomic DNA may be cut with one or more restriction enzymes so the ends are known but both embodiments allow greater flexibility in target selection than the embodiment shown in FIG. 3A because targets can be amplified from larger fragments that may not have been efficiently amplified without removal of a flap region.

In the embodiment shown in FIG. 3D the DNA can have both a 5' flap and a 3' flap. This allows for use of DNA that has ends that may have been generated by random shearing although restriction enzyme cut DNA may also be used.

In the first embodiment (shown in FIG. 3A) the ends of the fragments are known, and the probes are designed based on the known ends. In a preferred embodiment the ends are defined by restriction digestion. Once hybridized, perfect nicks will be formed and can be sealed by DNA ligase (including but not limited to T4 DNA ligase and Taq DNA ligase). This embodiment is the simplest functionally (see FIG. 4 and FIG. 5 for results of amplifications with perfect nicks), but is least flexible for selection of the targets. However, multiple cleavage enzymes can be used, either in separate cleavage reactions that are combined prior to hybridization of probes or in double digests, to increase the coverage of targets.

In the embodiment shown in FIG. 3B, the probes 303 may be designed so that the 5' end of target 302 forms a 5' flap structure when hybridized to 303. In a preferred embodiment the oligo 309 is designed so that it forms a single base 3' flap when hybridized to 103. See, Kao H-I et al., *J. Biol. Chem.* 277: 14379-14389, 2002. (FIG. 1B). A structure-specific flap nuclease may then be used to cleave the target at the position shown by the arrow. In preferred embodiments the flap nuclease may be, for example, the 5' to 3' exonuclease/endonuclease domain of a eubacterial DNA polymerases such as *E. coli* DNA polymerase and Taq DNA polymerase (Lyamichev V. et al., *Science* 260: 778-783; Kaiser et al., *J. Biol. Chem.* 274: 21387-21394, 1999), or the archeal or eukaryotic flap endonuclease 1 (FEN1), including murine FEN1 (Harrington J J and Lieber M R, *EMBO J.* 13: 1235-1246, 1994), yeast FEN1 (Harrington J J and Lieber M R, *Genes Dev.* 8: 1344-1355, 1994), human FEN1 (Hiraoka L R et al., *Genomics* 25: 220-225, 1995), *P. horikoshii* Pho FEN1 (Matsui E. et al., *J. Biol. Chem.* 274: 18297-18309, 1999), or Pfu FEN1 (Kaiser et al., *J. Biol. Chem.* 274: 21387-21394, 1999). These enzymes typically require a free 5' end and therefore, do not cleave at a mismatch or loop created during hybridization of dU probes and targeted sequences.

Figure 4:
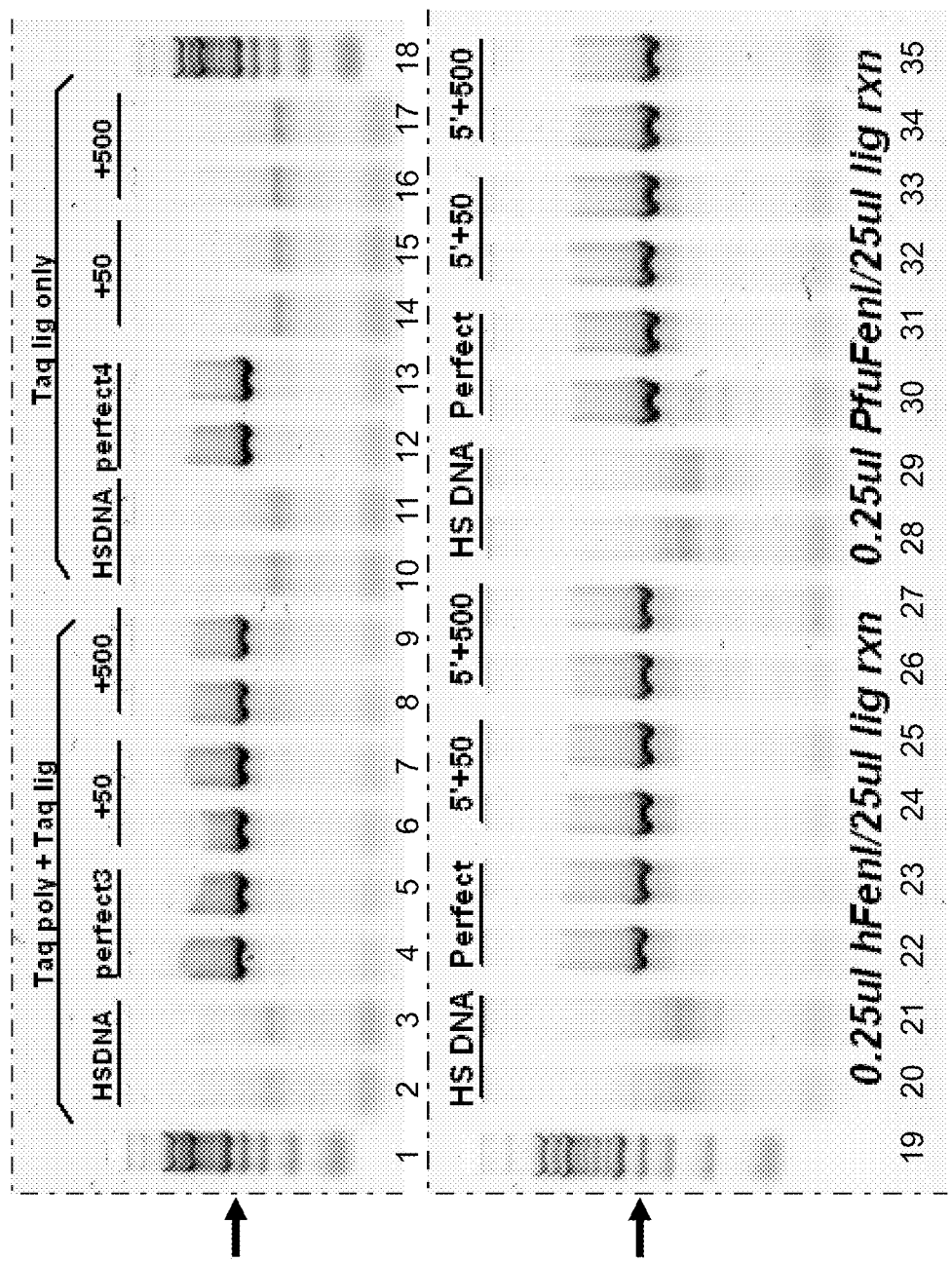
FIG. 4 Taq Polymerase and FEN1 specifically cleave the 5' flap to create nicks for ligation.
Figure 6:
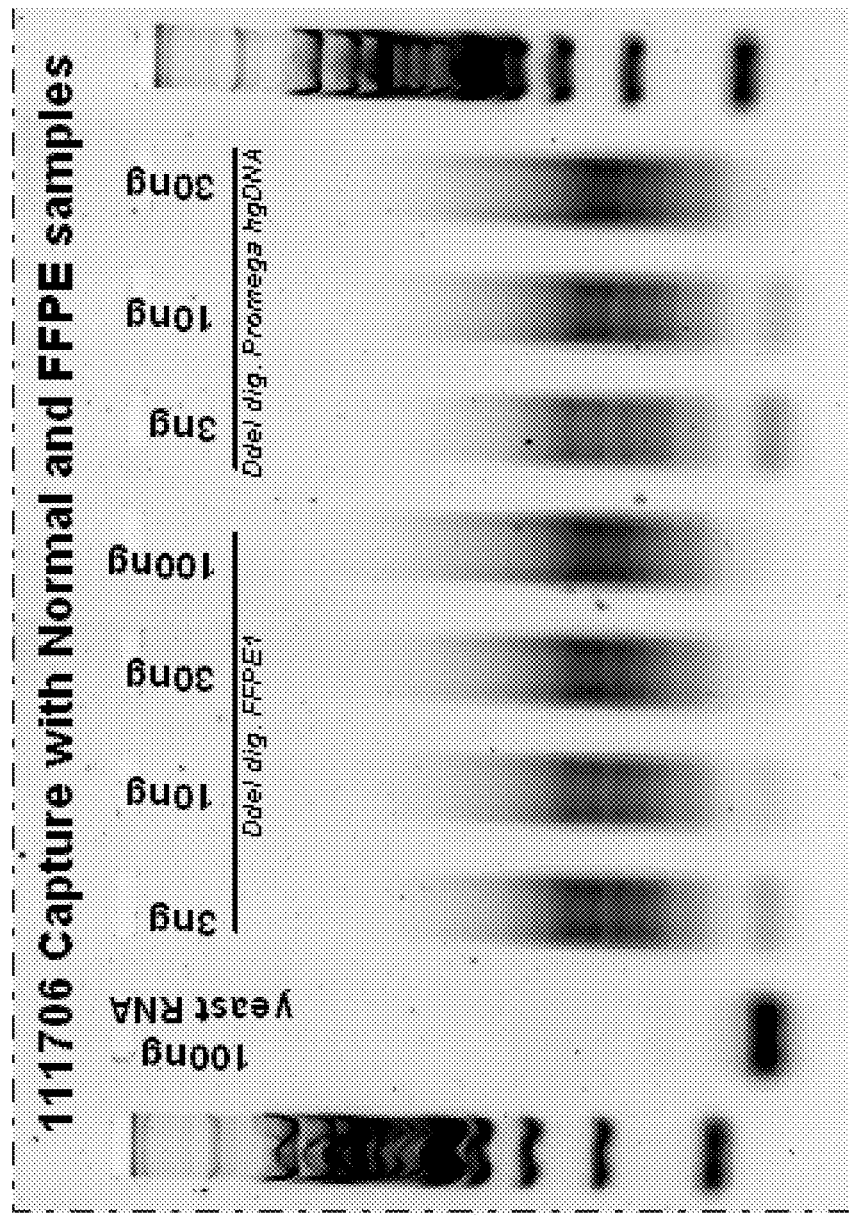
FIG. 6 shows specific amplification of 355 targets from a normal sample and an FFPE sample.
Figure 7:
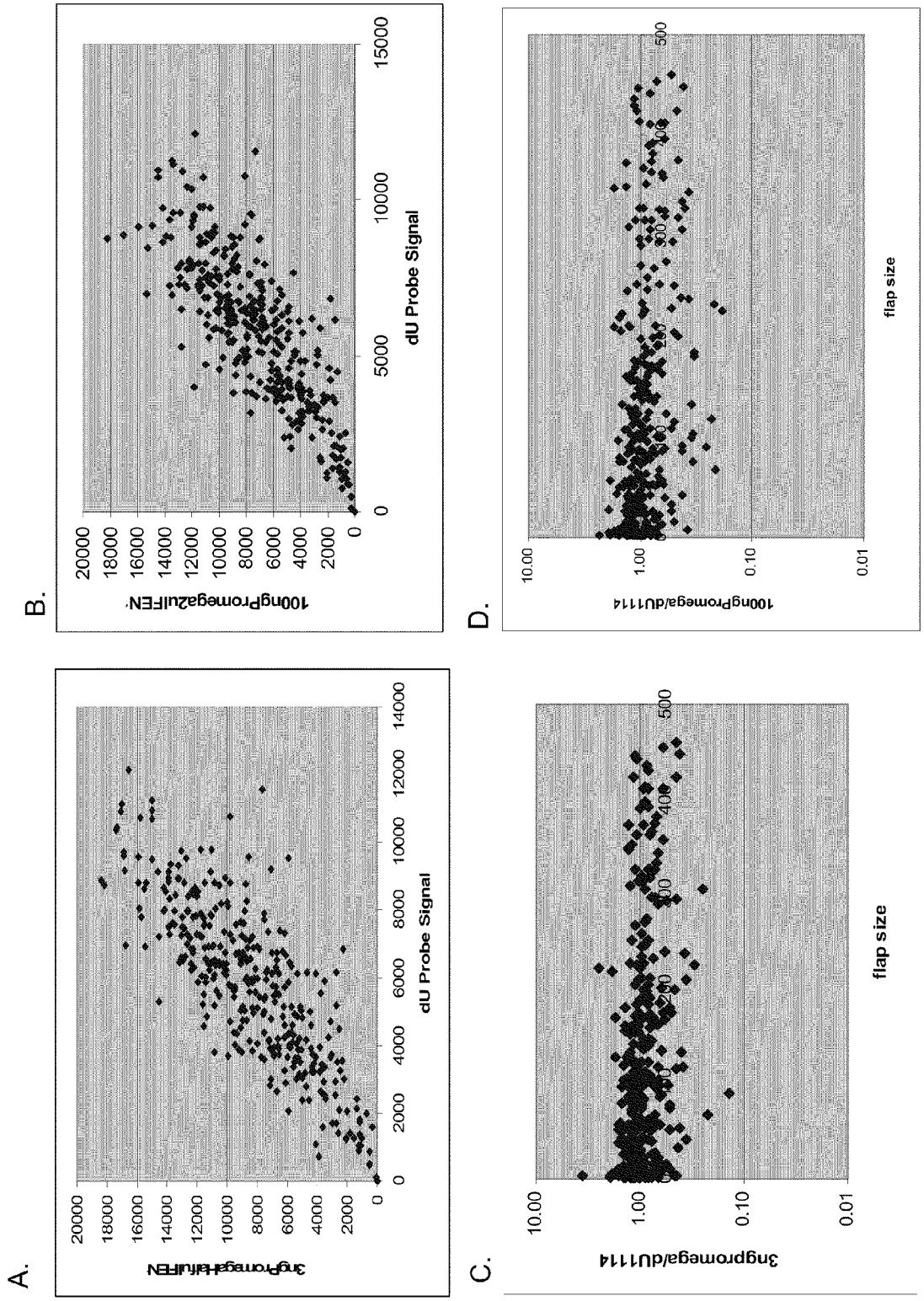
FIG. 7 shows array results of a dU-based multiplex PCR from normal genomic DNA.
Figure 8:
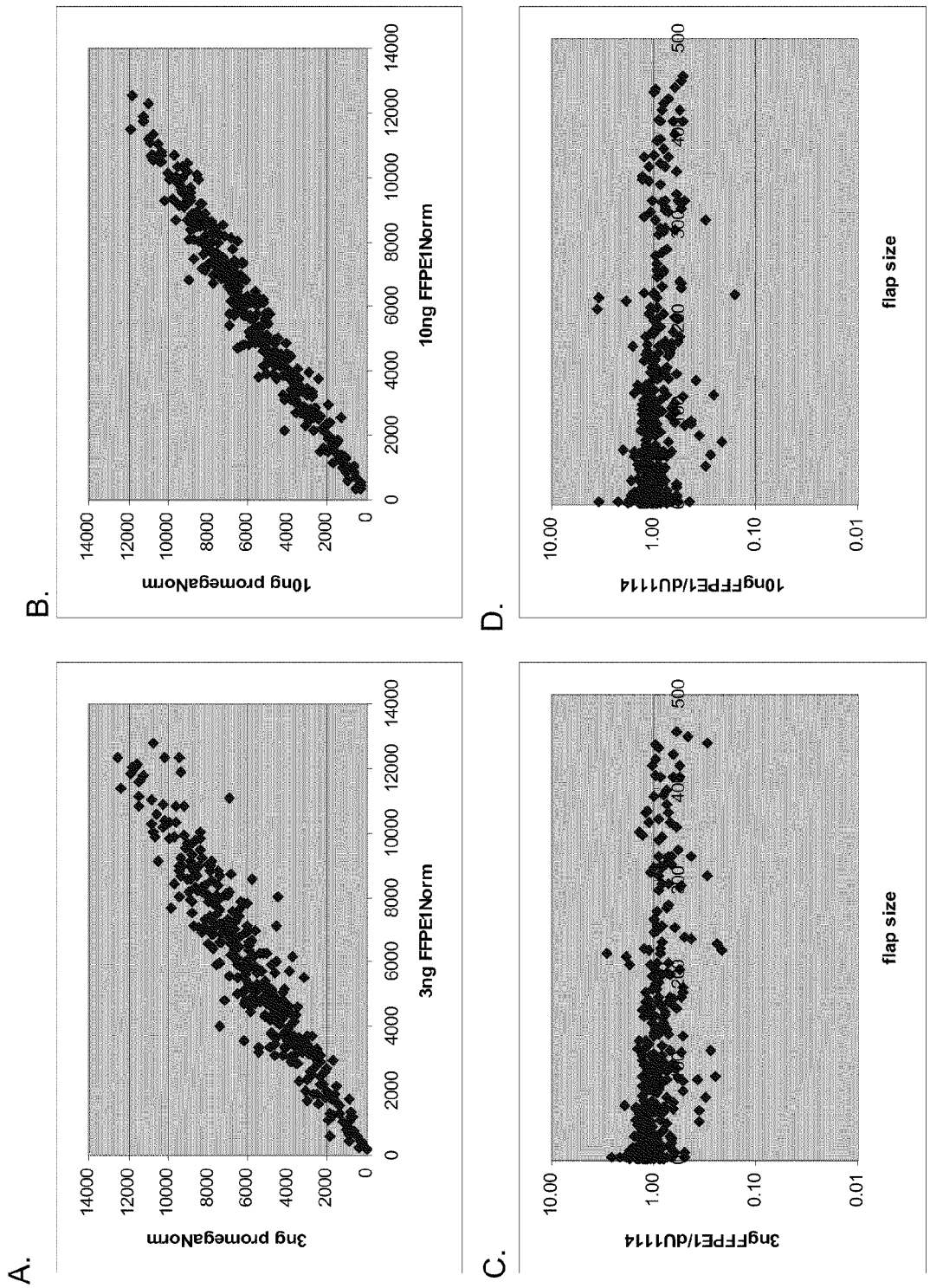
FIG. 8 shows a comparison of array results from FFPE samples and normal samples after capture.

For maximal specificity and activity, the probe and the oligo to be ligated to the 3' end of the target after removal of the flap are designed so that the 3'-end base of the 5' flap is the same base as the base at the 3' end of the oligo. This embodiment may be referred to as "double flap with 1 base 3' flap". As shown in FIG. 4 and example 1 below, both the 5' to 3' exo/endo-nuclease domain of the Taq DNA polymerase and human FEN1 can efficiently remove the 5' flap to create ligatable nicks. As described below in the Examples, A 355-plex amplification using DdeI restriction enzyme-digested human genomic DNA was performed and 100% of the targets were amplified successfully where an amplification of a specific target was successful if the ratio of multiplex PCR product to dU probes for that target was greater than 0.1) (FIGS. 6-8).

Although any single restriction enzyme may allow less than 100% coverage of a genome (coverage of ~85% of the human genome is obtained using DdeI restriction enzyme if 70-300 bp PCR amplicons are targeted with 5' flap lengths of up to 500 bases), use of two or three restriction enzyme separately may be used to increase the coverage to greater than about 85%, about 85 to 95% or about 95% to ~99%.

In another embodiment the target hybridized to the probe so the structure has a 3' flap, as shown in (FIG. 3C) ("nick 3' flap"). A 3' flap nuclease (also structure-specific) may be used, such as the human xeroderma pigmentosa complementation group F (XPF), (Sijbers A M et al., Cell 86: 811-822, 1996), Archeal *P. furiosus* helicase-associated endonuclease (Hef, Komori et al., Genes Genet. Syst. 77: 227-241, 2002), Archeal IXPF (Roberts J A et al., Mol. Microbiol. 48: 361-371, 2003) and Nar71 (Guy C P et al., Nucleic Acids Research 32: 6176-6186, 2004). See also, Matsui et al., *J Biol Chem* 274:18297-18309 (1999) for a description of FEN1 in *Pyrococcus horikoshii*.

The 3' flap nucleases may remove a few bases near the flap junction (generating a gap), and DNA polymerase and dNTPs may be used in step 319 to fill in the gap. In preferred aspects, less than all four different types of dNTPs may be included in the reaction (for example, only dATP and dCTP included) and the probes may be designed so that a gap of only one or two types of dNTP (for example, only dA or dC) is formed after 3' flap nuclease treatment.

In the most flexible embodiment (FIG. 3D), randomly fragmented DNA (for example, mechanically sheared, or chemically or enzymatically fragmented by an enzyme such as DNase or Apyrase) may be hybridized to the probes to generate flap structures at both ends (though some nick or gapped structures may also be present in the randomly sheared DNA). For the 5' flap, the same 1 base 3' flap in the oligo 309 is preferably included so the 5' flap nuclease such as human FEN1 can cut it efficiently and precisely to create a nick for ligation in step 321. For the 3' flap, a 3' flap nuclease such as XPF can be used simultaneously or sequentially.

In another embodiment double flap structures (as shown in FIG. 3D) are resolved without the use of a 3' flap nuclease. Many 3' flap nucleases can generate a gap and can also cut nick products efficiently, requiring that gaps be filled using a polymerase. This can be avoided by using a 3' to 5' ssDNA exonuclease in combination with a 5' flap nuclease, (instead of a 3' flap endonuclease) to remove a 3' flap in a double flap target.

In this embodiment, the probe is designed so the 3'-flap sequence near the junction will overlap with the 5'-end sequence of the nearby common oligo to create 2 to 8 bases of sequence that is identical in the 3' flap and the common oligo (GG to GGCGCGCC in the common oligo, for example). The repeated sequence is present at the junction between target and common sequence only once in the dU probe. The identical sequence does not have to be in the 5'-end of common oligo, but can be in the bases near the nick so a double flap structure will be created—a 5' flap from the end of the common oligo and the 3' flap from the target. The 3' to 5' ssDNA exonucleases such as exonuclease I, exonuclease T or exonuclease VII will degrade the ssDNA 3' flap, but will generally leave some blunt ends but mostly 3' extensions of a few bases. Because there area few overlapping bases at the ends and the ends will "breathe" a structure that has a 5' flap with 1 base of 3' flap will be generated at least some of the time, allowing removal of the 5' flap to create a perfect nick with high specificity and efficiency. The nick may be ligated by DNA ligase. Without the 3' to 5' ssDNA exonucleases, 5' flap nucleases such as FEN1, are unable to cut the 5' flap with a 3' flap of more than 1 base (Kao H-I et al., J. Biol. Chem. 277: 14379-14389, 2002).

In some embodiments, because genomic DNA or cDNA is used directly, the resulting amplification products will be proportionate to the starting copy amount of individual targets, allowing the quantitation of copy number of genomic DNA or expression level of cDNA. Also contemplated are computer implemented methods for selecting target sequences with overlapping sequence regions with the common oligo.

The use of 5' flap nucleases and 3' to 5' ssDNA exonucleases to create nick products from double flap structures may be combined with other strategies to provide a powerful strategy for multiplex targeted amplification. In one aspect the methods are applied to the selector-guided multiplex amplification of Dahl et al., Nucleic Acids Res. 33: e71, 2005). In this method, a synthetic oligo with two specific sequence (from the same strand of DNA separated by ~70-1000 bases, for example) separated by a common sequence in the middle of the oligo is used. Random sheared genomic DNA may be hybridized to this oligo, creating a circle of the target after removal of the 5' flaps and 3' flaps.

In another embodiment, where a 5' flap nuclease is used, a 5' to 3' ssDNA exonuclease, such as RecJ or Exo VII (which contains both 5' to 3' and 3' to 5' exonuclease activities), may be used to shorten the length of the 5' flap. By doing this, the efficiency of the removal of long 5' flaps (for example, greater than 50 bases) may be increased, since the removal efficiency is dependent on flap length, although very good cleavage can be obtained up to at least 500 bases in most cases. (See FIG. 7 and FIG. 8). In another aspect Dna2 may be used to shorten the 5' and 3' flaps. See Kim et al., *Nucleic Acids Res.* 34:1854-1864 (2006) and Stewart et al. JBC 281:38565-38572 (2006). The lengths of the flaps may be, for example, 1 to 500 bases or 1 to 1,000 bases. The length of the targets to be amplified may be about 100 to 1,000 or 2,000 bases, but the targets may be longer, for example, 2,000 to 10,000 baspairs.

Once the targeted DNAs are captured and ligated to common oligos, the dU probes may be degraded with uracil-DNA glycosylase (UDG or UNG) plus heat treatment or treatment with an AP endonuclease, and the targeted DNAs may be amplified with common PCR primers.

Figure 5:
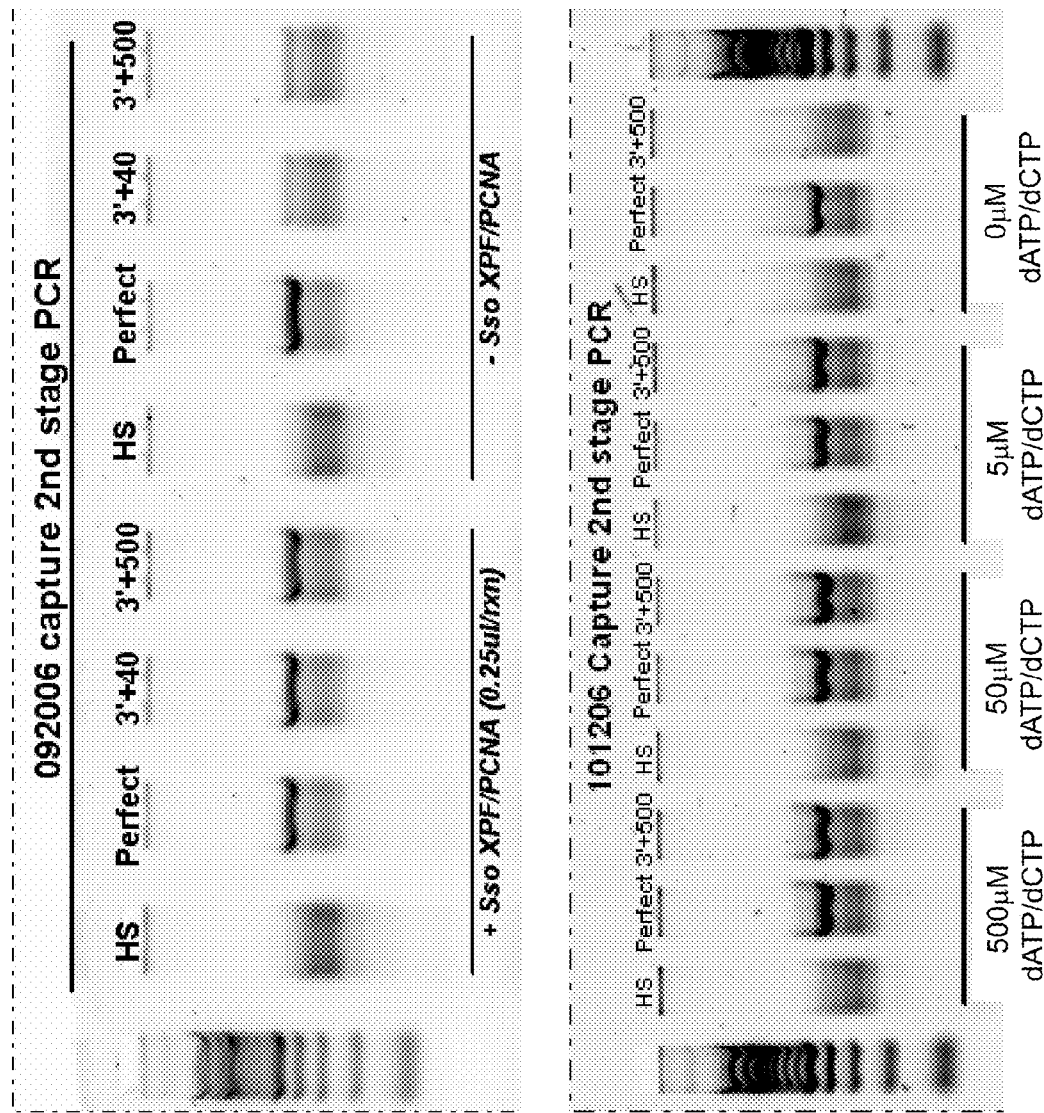
FIG. 5 shows gel separation of the products of removal of a 3' flap by Sso XPF/PCNA mix.

Several aspects of the multiplex PCR process described below could also be used to increase the sensitivity and efficiency and make the assay easier and more robust. For example, since many other proteins interact with 5' or 3' flap nucleases, the efficiency of flap removal or activity of the flap nucleases can be increased by addition of one or more adjunct proteins. One such proteins is proliferating cell nuclear antigen (PCNA), which has been demonstrated to increase the activity of human FEN1 by up to 50 fold. Furthermore, Sso PCNA is required for the 3' flap removal activity of Sso XPF. FIG. 5 shows that using Sso XPF in the presence of PCNA functions to remove a 3' flap of 40 or 500 bases.

In another embodiment a fused oligo, (C1C2) consisting of both common sequences C1 and C2 as a single contiguous oligo, may be used. After hybridization, enzymatic treatment and ligation, the specific targeted sequences will be circularized with the fused C1C2. This approach allows the removal of the DNA that hasn't been circularized (for example, the original targeted DNA and the probes) by treatment with DNA exonuclease. Exonucleases that may be used include, for example, exonuclease I, exonuclease VII, exonuclease III and T7 exonuclease. The circular sequence can be opened with UDG if one or more dU is included in the common C1C2 oligo while the dU probes are also degraded, and amplified with common PCR primers. Alternatively, circular DNAs can be amplified with minimal bias using Phi29 and random primers or a primer to C1C2. Rolling circle amplification (RCA) may be used. For a description of rolling circle amplification see, for example, U.S. Pat. Nos. 6,183,960 and 6,210,884 to Lizardi and U.S. Pat. No. 6,593,086 to Zhang. See also, Fire and Xu, Proc. Natl. Acad. Sci. USA 92:4641-4645 (1995), Zhang, D Y, et al., Gene, 211(2): 277-285, 1998 and Lizardi, P M, et al., Nature Genetics, 19: 225-232, 1998. See also Kumar U.S. Pat. No. 5,912,124.

Commercial available kits containing phi 29 enzymes and random primer pools can be used. Alternatively, the same probe pool can be used with Phi29 to produce the products. These multiplex amplified products can be used directly in many applications, especially resequencing by tiling array or genotyping.

Circular double-stranded DNA may not form efficiently for smaller sizes, although as small as 70 bp "mini plasmids" have been reported. The circularization method may also be of reduced efficiency due to the formation of linear structures instead of circularized structures. Efficiency may be improved by denaturing the double stranded linear dU probes and making circlular ssDNA dU probes using CIRCLI-GASE™ ssDNA ligase from EpiCentre Biotechnologies (Madison, Wis.). The circular ssDNA dU probes may be used to capture targeted DNA.

In one embodiment solid-phase dU capture is used instead of solution-based capture. For example, one of the dU probe strands can be linked to biotin and can be immobilized to a tube coated with streptavidin or to magnetic beads coupled with streptavidin. One limitation is the space restriction created which could lead to lower efficiency. The solid-phase capture allows the removal and exchange of the buffer/reagents conveniently without desalting or purification steps.

To minimize the unwanted cleavage of nick structures by 5' flap nucleases and 3' flap nucleases before ligation, the 5'-end or 3'-end of the common oligos used in capture may include one or more phosphorothioate bonds. The phosphorothioate bond is resistant to most exonucleases (Putney S D et al., Proc. Natl. Acad. Sci. USA 78: 7350-7354, 1981; Skerra A, Nucleic Acids Res. 20: 3551-3554, 1992) and potentially the structure-specific flap nucleases also.

The key advantages of the disclosed methods of multiplex PCR are that they have high sensitivity and specificity and can be scaled up to amplify larger number of targets, for example, more than 10,000-plex, 50,000-plex or 100,000-plex. It has been demonstrated that 3 ng human genomic DNA (~1000 copies) can be used to amplify the amplicons with 100% success rate (ratio of >0.1, FIG. 7). Similar amounts of genomic DNA, based on TAQMAN™ real time PCR quantitation (Applied Biosystems), from formalin fixed paraffin embedded tissue (FFPE) was also amplified equally well (FIG. 8), opening up an opportunity to selectively amplify these and other degraded DNA efficiently and in highly multiplexed reactions (100 to 100,000-plex). These multiplex amplified products can be used directly in many applications, especially for downstream mismatch repair detection (MRD) or resequencing by tiling array or genotyping. MRD is disclosed in U.S. Pat. Nos. 7,153,652, 6,709,827 and 6,406,847, which are incorporated herein by reference for all purposes. In one embodiment the methods may be used for the preparation of targets used in resequencing analysis using GENE-CHIP CUSTOMSEQ® arrays.

In some embodiments kits for multiplex amplification are disclosed. Kits may include, for example, reagents and arrays for resequencing or genotyping applications. The kits may include, for example, dU probes, a flap endonuclease, a DNA polymerase, common oligonucleotides that may include nuclease resistant linkages, primers for PCR, buffers, and control DNA. The kits may also include arrays and instructions for performing one or more of the methods disclosed herein. For each target to be amplified a different dU probe may be included. The kit may include, for example, 100, 500, 1,000, 2,000 or 10,000 to 500, 1,000, 2,000, 10,000, 20,000, 50,000 or 100,000 different dU probes.

In the examples below the multiplex strategy with 5' flap nuclease has been shown to work very well with 355-plex and should be scalable to much higher levels of multiplexing (1,000 to 100,000 or higher). Employing a strategy that uses a 5' flap nuclease only has the limitation that less than 100% of an entire genome can be targeted because of the requirement for use of restriction enzymes. Embodiments that use random sheared genomic DNA with both 5' and 3' flaps may be used to obtain 100% coverage and high flexibility in designing the probes. The methods do require generation of dU probes corresponding to the targets, but once the dU probe is made, it can be re-amplified to generate large amounts of stable probe that can be used for many multiplex PCR. In general, the dU probe need be synthesized and amplified only once.

In one aspect target sequences from a nucleic acid sample are amplified by fragmenting the nucleic acid sample to obtain fragments; adding to the fragments a plurality of dU probes to the complex mixture, wherein there is a dU probe for each target sequence and wherein each dU probe comprises: (i) a central target region that is complementary to a target sequence; (ii) a 5' first common sequence; (iii) a 3' second common sequence. Adding to the mixture a first oligonucleotide that is complementary to the first common sequence and a second oligonucleotide that is complementary to the second common sequence. Adding a 5' flap nuclease, at least one species of dNTP, a 3' flap nuclease, a DNA ligase and a DNA polymerase to the mixture of (b) to form targets ligated to the first and second common oligonucleotides. Adding a uracil DNA glycosylase to the mixture above and cleaving the dU probes. Then amplifying the targets ligated to the first and second common oligonucleotides using primers to the first and second common sequences.

In one aspect, a plurality of nucleic acid targets of distinct sequence are amplified. In a first step a first oligonucleotide and a second oligonucleotide are appended to each of the nucleic acid targets by annealing each target and a respective first oligonucleotide to a respective probe from a plurality of probes in a reaction mixture, wherein each probe comprises a first region of complementarity to a respective one of said targets, a first oligo positioning region directly adjacent thereto, the nucleotide of the template complementarity region and the nucleotide of the first oligo positioning region that are directly adjacent within said probe being first junctional nucleotides that define a first probe junction, and a second oligo positioning region directly adjacent to the first template complementarity region, the nucleotide of the template complementarity region and the nucleotide of the second oligo positioning region that are directly adjacent within said probe being second junctional nucleotides that define a second probe junction, and wherein each said first oligonucleotides includes a first common priming sequence and a region that is complementary to the first oligonucleotide positioning region of the probe. Then creating a first ligatable free end at the nucleotide of each template that is annealed to the junctional nucleotide of its respective probe's first target complementarity region, wherein each of said ligatable free ends is created by removing target regions that are noncomplementary to said probe first complementarity region by a flap endonuclease. The next step is ligating each first oligonucleotide to its respective target first free end to append the first oligonucleotide to its respective target within the plurality of nucleic acid targets and appending a second oligonucleotide to each of the plurality of targets of distinct sequence by: annealing a respective second oligonucleotide to each probe concurrently with annealing of the target to the probe, wherein the second oligonucleotide includes a terminal region that is complementary to the second oligonucleotide positioning region of its respective probe and a second common sequence, the terminal nucleotide of said terminal oligonucleotide region being annealed to the junctional nucleotide of the probe's second oligonucleotide positioning region. The next step is creating a second ligatable free end at the target nucleotide that is annealed to the second junctional nucleotide of the probe's first target complementarity region; and then ligating the second oligonucleotide to the target second free end. The next step is separating the targets, after ligation, from the probes and the oligonucleotides and then amplifying a region of each target by PCR using primers to the common sequence.

In one aspect, the amplified targets may be used for resequencing using the Affymetrix resequencing arrays, for example, the CUSTOMSEQ™ resequencing array. Resequencing arrays allow variation detection in a sequence of interest by tiling probes for all possible single nucleotide variations within the sequence. They have been used in a number of studies. See, for example, Cutler et al., Genome Res. 11:1913-25 (2001), Lipkin et al., Nature Genet. 36:694-699 (2004), Zwick et al., Genome Biol 6:R10, (2005) and Warrington et al., Hum Mutat 19:402-9 (2002). Resequencing arrays are currently commercially available for analysis of up to 300 kb of double stranded DNA (600,000 bases total). Arrays can be purchased for 50 kb or 100 kb as well. Larger sequences can also be analyzed. The amplification methods disclosed herein can be used in place of the long range PCR amplification methods currently used for resequencing, eliminating the need to normalize and pool amplicons prior to hybridization. In some aspects kits for amplification to prepare targets for resequencing are disclosed. The amplification products may be fragmented and labeled by standard methods prior to hybridization to arrays.

In many aspects of the presently described methods a flap endonuclease is used to remove overhanging ends prior to ligation of the ends of the target DNA. Flap endonucleoases (FEN-1) have been described in a number of organisms including mouse, human, yeast and a number of thermophilic organisms. They are structure-specific endonucleases that cleave 5' flap structures endonucleotyltically and have a double-strand-specific 5'-3' exonuclease activity. The exonuclease activity utilizes double-stranded DNA with a nick or gap, and the endonuclease activity requires a flap structure. In prokaryotes the FEN 1 activity is the 5' nuclease domain of DNA polymerase I. There is a separate polypeptide in eukaryotes, archaea and some bacteriophage. For additional information about different enzymes and substrate specificities, see, Xu et al., *J. Biol. Chem.* 276:30167-30177 (2001) and Kaiser et al. *J Biol Chem* 274:21387-21394 (1999). FENs catalyze hydrolytic cleavage of the phosphodiester bond at the junction of single and double stranded DNA (see, Harrington and Lieber, EMBO 13:1235-46 (1994); Harrington and Lieber, J Biol Chem 270:4503-8 (1995)). In cells, FEN-1 is one of the enzymes required for lagging strand DNA replication and in particular, the maturation of Okazaki fragments by generation of ligatable nicks. Flap endonuclease activities are used, for example, in the TAQMAN assay and in the INVADER assay. Taq DNA polymerase I endonucleolytically cleaves DNA substrates, releasing unpaired 5' arms of bifurcated duplexes. See Lyamichev et al., PNAS 96:9143 (1999) and Lyamichev et al., *Science* 260: 778-783 (1993).

The targets may be selected for analysis of a variety of genetic and epigenetic features. The target regions may contain known polymorphic regions and the amplified targets are analyzed to determine the genotype of the sample at the polymorphic regions. In another aspect the methods are combined with methods for analysis of methylation, for example, the targets may be treated with bisulfite prior to amplification so that methylation dependent modifications are made to the sequence and those changes are maintained in the amplification product and can be detected as changes in the sequence. Methylation detection using bisulfite modification and target specific PCR have been disclosed, for example, in U.S. Pat. Nos. 5,786,146, 6,200,756, 6,143,504, 6,265,171, 6,251,594, 6,331,393, and 6,596,493.

Prior to hybridization to the dU probes, the nucleic acid sample containing the targets may be treated with bisulfite. During bisulfite treatment, unmethylated cytosine is converted to uracil and methylated cytosine remains cytosine. See Clark et al., Nucleic Acids Res., 22(15):2990-7 (1994). When the modified strand is copied a G will be incorporated in the interrogation position (opposite the C being interrogated) if the C was methylated and an A will be incorporated in the interrogation position if the C was unmethylated. This results in a detectable sequence difference between methylated and unmethylated positions. The methods disclosed herein may be combined with the methods disclosed in U.S. application Ser. No. 11/923,649 filed Oct. 24, 2007.

Kits for DNA bisulfite modification are commercially available, for example, Human Genetic Signatures' Methyleasy and Chemicon's CpGenome Modification Kit. See also, WO04096825A1, which describes bisulfite modification methods and Olek et al. Nuc. Acids Res. 24:5064-6 (1994), which discloses methods of performing bisulfite treatment and subsequent amplification on material embedded in agarose beads. In one aspect a catalyst such as diethylenetriamine may be used in conjunction with bisulfite treatment, see Komiyama and Oshima, *Tetrahedron Letters* 35:8185-8188 (1994). See also, Hayatsu et al, *Proc. Jpn. Acad.* Ser. B 80:189-194 (2004) for alternative procedures.

Bisulfite treatment allows the methylation status of cytosines to be detected by a variety of methods. For example, any method that may be used to detect a SNP may be used, for examples, see Syvanen, Nature Rev. Gen. 2:930-942 (2001). Methods such as single base extension (SBE) may be used or hybridization of sequence specific probes similar to allele specific hybridization methods. In another aspect the Molecular Inversion Probe (MIP) assay may be used. The MIP assay is described in Hardenbol et al., *Genome Res.* 15:269-275 (2005) and in U.S. Pat. No. 6,858,412.

The methods may also be used for analysis of copy number. See, for example Wang et al., *Nucleic Acids Res.* 33:e183 (2005) and Ji et al., *Cancer Res.* 66:7910-9 (2006). In other aspects the methods may be used to analyze targets from compromised samples, for example, formaldehyde fixed and paraffin embedded (FFPE) samples or degraded samples. In many embodiments the amplification products may be analyzed by hybridization to an array of probes. Preferred arrays include those commercially available from Affymetrix, Inc. and include tiling arrays, gene expression arrays, mapping arrays (10K, 100K, 500K, SNP 5.0 and SNP 6.0), promoter arrays and tag arrays. The amplification products may also be analyzed by hybridization to arrays of oligonucleotides attached to beads or other solid supports.

In another aspect the amplification products may be analyzed by sequencing methods such as those marked by Roche/454, Helicose, Illumina/Solexa, and ABI (SOLID) and others.

EXAMPLES

Example 1

Taq Polymerase and FEN1 specifically cleave the 5' flap to create nicks for ligation. A control dU probe and corresponding targets with different flap length (0, 50 or 500 bases) were generated by PCR and purified. 50 amol of each were hybridized for about 3 hours in 30 mM Tris-HCl, pH 7.9, 15 mM $MgCl_2$, 0.1% BSA by step-wise annealing (70° C. 40 min, 65° C. 40 min, 60° C. 40 min, 55° C. 20 min, 50° C. 20 min and then 4° C. hold after denaturation at 94° C. for 5 min. The reaction was desalted, the 5' flap was removed and the targets were ligated using 40 U Taq ligase plus either 5 U Taq DNA polymerase, 0.25 µl hFEN1 or 0.25 µl Pfu FEN1 or none. After ligation, the reactions in the upper panel were purified by QIAQUICK™ spin columns (QIAGEN). All ligation products were treated with UDG, then amplified with common primers. An aliquot of each was separated by gel electrophoresis as shown in FIG. 4.

The expected position of migration of the expected product is shown by an arrow in both the upper and lower panels. DNA ladders are shown in lanes 1, 18, and 19. Negative controls of herring sperm DNA are shown in lanes 2, 3, 10, 11, 20, 21, 28 and 29. Lanes 2 to 9 were treated with Taq polymerase and Taq ligase, lanes 10 to 17 were treated with Taq ligase only, lanes 20 to 27 were treated with 0.25 µl hFEN1 and ligase and lanes 28 to 35 were treated with 0.25 µl PfuFEN1 and ligase. As expected, a product of the expected length is observed in lanes 4-9, 12, 13, 22-27 and 30-35. The probe generated structures in lanes 14-17 are designed to have 5' overhangs of 50 (14 and 15) or 500 bases (16 and 17) and are not expected to result in amplifiable product in the absence of a 5' flap nuclease. As expected no amplified product is observed in these lanes or in the negative control lanes with just herring sperm DNA. Lanes 4, 5, 12, 13, 22, 23, 30 and 31 have probes, targets and oligos that hybridize to generate nicks that are ligatable without cleavage of 5' flaps so product is observed in all of these lanes, even in lanes 12 and 13 that do not have added 5' flap nuclease.

Example 2

FIG. 5 shows that a 3' flap structure as shown in FIG. 3C can be removed by Sso XPF/PCNA mix (kindly provided by Dr. Malcolm White, UK) so that the common oligos can be ligated to the ends of the target and the target amplified by PCR. The reaction conditions were those used in Example 1 except different 3' flap lengths were tested with 0.25 µl Sso XPF/PCNA, 40 U Taq DNA ligase, 2.5 U Taq DNA polymerase, 300 µM each of dATP and dCTP (the 5 bases next to the ligation site in the 3' flap position) for the upper panel. The reactions in the lower panel had 0.25 µl Sso XPF/PCNA, 40 U Taq DNA ligase, 2.5 U Taq DNA polymerase, and varying amounts of dATP and dCTP as indicated. The template was either herring sperm DNA (HS), a target without 5' or 3' flaps (perfect), a target with a 3' flap of 40 bases (3'+40) or a target with a 3' flap of 500 bases (3'+500). The amplification product is not observed in the lane where there is no added dATP/dCTP and the 3'+500 lane. This is likely because the 3' flap endonuclease removes some of the bases near the nick generating a gap that can be filled in by DNA polymerase in the presence of the appropriate dNTPs. The structure of the probe-target complex is analogous to that shown in FIG. 3C.

Example 3

FIG. 6 Specific amplification of 355 targets simultaneously from normal control genomic DNA (Promega) and an FFPE human genomic DNA. Genomic DNA was cut with DdeI and 3 ng-100 ng was used in direct multiplex PCR with a dU probe pool (50 amol each) in 20 µl volume. To prepare the dU probe pool individual PCR reactions, in the presence of dUTP, were performed for each of 384 targets and successful products were obtained for 370 of the 384 (in subsequent studies PCR amplification conditions that allow successful amplification of the remaining 14 have been identified). 369 of the dU probes were used for capture (one was excluded because it contained a highly repetitive Alu sequence. The dU probes and digested DNA were mixed in a hybridization reaction with the common oligos first to allow hybridization of the dU probes, the targets and the oligos and to allow flap formation. The FEN1 and ligase were added after the hybridization step. These steps may also be combined if a thermostable FEN1 is used and denaturation, annealing, flap removal and ligation can be cycled. After the ligation and flap removal the dU probes are degraded using uracil-DNA glycosylase followed by heating at 95° C. Then the targets are amplified by PCR using the common primers. The far left lane and far right lane are 100 bp markers (NEB). The specific PCR sizes are from 145-375 bp. Notice that no background was seen in 100 ng yeast RNA which was used as a carrier except a nonspecific band below 100 bp.

FIG. 7 shows the results of array analysis of dU-based mPCR products from FIG. 6. Either 0.5 µl (1.5 U) or 2 µl (6 U) of human FEN1 (Trevigen) was used for 3 or 100 ng human genomic DNA (Promega) digested with DdeI. Panels A and C are 3 ng human genomic DNA, 0.5 µl FEN1, B and D are 100 ng DNA and 2 µl FEN1. Panels C and D show flap size on the X axis and ratio of the signal from the DdeI fragmented DNA with FEN to a control dU amplification on the y-axis (control is the starting dU probe pool fragmented, labeled and hybridized to a copy of the same array). The ratio was greater than 0.1 for all targets in both C and D indicating 100% success for the amplification. After amplification, the PCR products were purified, fragmented and end labeled. The labeled fragments were hybridized to a custom resequencing array (Kinaser520379_7G) according to the Custom Resequencing protocol. The dU probe pool was fragmented, labeled and hybridized to the array as a control.

FIG. 8 shows comparison of the targets amplified from FFPE DNA in FIG. 6 to the amplification products from human genomic DNA (also from FIG. 6). The results show that efficient mPCR amplification can be obtained using 0.5 µl human FEN1 and 3 ng DNA from an FFPE sample. Each target was amplified from the FFPE samples with about the same signal as from the normal DNA (panels A and B). All of the targets were amplified from both the 3 ng and 10 ng FFPE samples with a ratio to dU1114 that was greater than 0.1 (see panels C and D). The samples are those shown in FIG. 6.

Additional genotyping methods are disclosed in Wang H-Y et al. (2005) Genome Res. 15: 276-283 and Faham M. et al. (2005) Proc. Natl. Acad. Sci. USA 102: 14712-14722. Multiplex amplification methods that can be used in combination with the disclosed methods are described in Dahl et al. (2005), Shapero et al., (2001) Genome Res. 11: 1926-1934, Shapero et al. (2004) Nucleic Acids Res. 32: e181 and Pemov et al. (2005) Nucleic Acids Res. 33: el1.

Yeast flap endonuclease is described in Kao H I et al. (2002). J. Biol. Chem. 277: 14379-14389. A method for using the 5' to 3' exonuclease activity of Taq DNA polymerase is described in Holland P M et al. (1991) Proc. Natl. Acad. Sci. USA 88: 7276-7280.

Nucleases that may be used in combination with the methods disclosed herein are described in Guy et al (2004) Nucleic Acids Res. 32: 6176-6186, Nishino et al. (2006) 16: 60-67, Matsui et al. (2004) J. Biol. Chem. 279: 16687-16696, Komori et al. (2002) Genes Genet. Syst. 77: 227-241, Roberts et al., (2003) Mol. Microbiol. 48: 361-371, Sijbers A M et al. (1996) Cell 86: 811-822, Hiraoka L R et al. (1995) Genomics 25: 220-225, Harrington J J and Lieber M R (1995) J. Biol. Chem. 270: 4503-4508, Harrington J J and Lieber M R (1994) EMBO J. 13: 1235-1246 (endonuclease), Kaiser M W et al. (1999) Biol. Chem. 274: 21387-21394 (exonuclease), Lyamichev et al. (1993) Science 260: 778-783 (endonuclease), and Liu et al., (2004) Annu Rev. Biochem. 73: 589-615 (Flap endo 1).

CONCLUSION

It is to be understood that the above description is intended to be illustrative and not restrictive. Many variations of the invention will be apparent to those of skill in the art upon reviewing the above description. The scope of the invention should be determined with reference to the appended claims, along with the full scope of equivalents to which such claims are entitled. All cited references, including patent and non-patent literature, are incorporated herewith by reference in their entireties for all purposes as if each had been individually and specifically incorporated by reference herein.

---

We claim:

1. A method for amplifying target sequences within a nucleic acid sample, the method comprising:
   fragmenting the nucleic acid sample with a restriction enzyme, thereby producing a fragmented nucleic acid sample comprising one or more target sequences;
   adding circularization probes to the fragmented nucleic acid sample, wherein each circularization probe comprises a first probe region and a second probe region, wherein the first and second probe regions are respectively complementary to a first target region and a second target region of one of the target sequences, and wherein the circularization probes hybridize with target sequences to form probe-target structures in which each target sequence includes a flap of two or more bases at the 5' end and a flap of one base at the 3' end;
   removing the 5' flaps with a 5' flap nuclease, thereby generating probe-target structures in which each target sequence includes a 5' end juxtaposed with the 3' end, with the 5' end and the 3' end separated by a nick;
   ligating the 5' ends to the juxtaposed 3' ends of the target sequences to circularize the target sequences; and
   amplifying the circularized target sequences.

2. The method of claim 1, wherein the 5' flap nuclease is selected from the group consisting of *E. coli* DNA polymerase, Taq DNA polymerase and flap endonuclease 1.

3. The method of claim 1, wherein each 5' flap includes a 3' end base that is identical to the one base of the 3' flap of the same target sequence.

4. A method for amplifying target sequences within a nucleic acid sample, the method comprising:
   fragmenting the nucleic acid sample with a restriction enzyme, thereby producing a fragmented nucleic acid sample comprising one or more target sequences;
   adding circularization probes to the fragmented nucleic acid sample, wherein each circularization probe comprises a first probe region and a second probe region, wherein the first and second probe regions are respectively complementary to a first target region and a second target region of one of the target sequences, and wherein the circularization probes hybridize with target sequences to form probe-target structures in which the target sequences include 3' flaps of two or more bases and 5' ends perfectly complementary to a corresponding first probe region,
   removing the 3' flaps with a 3' flap nuclease, wherein removing the 3' flap forms a 3' end of the target sequence that is separated from the 5' end of the target sequence by a gap;
   extending the 3' ends of the target sequences with DNA polymerase and dNTPs to fill in the gaps, wherein the dNTPs comprise only two of dATP, dCTP, dGTP and dTTP:
   ligating the 3' ends to the 5' ends of the same target sequences to circularize the target sequences; and
   amplifying the circularized target sequences.

5. The method of claim 4, wherein the 3' flap nuclease is selected from the group consisting of *Xeroderma pigmentosa* complementation group F, *P. furiosus* helicase associated endonuclease, *S. solfataricus* XPF and Nar71.

6. The method of claim 4, wherein the dNTPs comprise only dATP and dGTP.

7. The method of claim 1, wherein the 5' flap nuclease is a 5' flap endonuclease, and wherein removing the 5' flaps with a 5' flap nuclease additionally comprises:
   shortening the 5' flaps with a ssDNA exonuclease, wherein the ssDNA exonuclease has 5' to 3' exonuclease activity.

8. The method of claim 7, wherein the 5' flaps are more than 50 bases in length.

9. The method of claim 7, wherein the ssDNA exonuclease is selected from the group consisting of RecJ and exonuclease VII.

10. The method of claim 1, further comprising digesting non-circularized nucleic acids with an exonuclease, wherein said digesting is performed after circularizing the target sequences but before amplifying the circularized target sequences.

11. The method of claim 10, wherein the exonuclease is selected from the group consisting of exonuclease I, exonuclease VII, exonuclease III, and T7 exonuclease.

12. The method of claim 1, wherein amplifying the circularized target sequences does not involve PCR amplification.

13. The method of claim 1, wherein amplifying the circularized target sequences is performed by rolling circle amplification.

14. The method of claim 1, wherein the fragmented nucleic acid sample includes 100 to 50000 different target sequences.

15. The method of claim 1, wherein the circularization probes are 6 to 60 bases in length.

16. The method of claim 15, wherein the circularization probes are about 12 to about 40 bases in length.

17. The method of claim 1, wherein the circularization probes are about 40 bases in length.

18. The method of claim 1, wherein each circularization probe consists of a first probe region and a second probe region.

19. The method of claim 4, wherein each circularization probe consists of a first probe region and a second probe region.

* * * * *